(12) United States Patent
Hirokawa et al.

(10) Patent No.: US 12,051,197 B2
(45) Date of Patent: Jul. 30, 2024

(54) IMAGE PROCESSING METHOD, IMAGE DISPLAY METHOD, IMAGE PROCESSING DEVICE, IMAGE DISPLAY DEVICE, IMAGE PROCESSING PROGRAM, AND IMAGE DISPLAY PROGRAM

(71) Applicant: NIKON CORPORATION, Tokyo (JP)

(72) Inventors: Mariko Hirokawa, Yokohama (JP); Yasushi Tanabe, Fujisawa (JP)

(73) Assignee: NIKON CORPORATION, Tokyo (JP)

( * ) Notice: Subject to any disclaimer, the term of this patent is extended or adjusted under 35 U.S.C. 154(b) by 318 days.

(21) Appl. No.: 17/417,970

(22) PCT Filed: Dec. 28, 2018

(86) PCT No.: PCT/JP2018/048578
§ 371 (c)(1),
(2) Date: Jun. 24, 2021

(87) PCT Pub. No.: WO2020/136900
PCT Pub. Date: Jul. 2, 2020

(65) Prior Publication Data
US 2022/0076412 A1    Mar. 10, 2022

(51) Int. Cl.
*G06T 7/00*   (2017.01)
*A61B 3/00*   (2006.01)
*A61B 3/10*   (2006.01)
*A61B 3/12*   (2006.01)
*G06T 7/11*   (2017.01)
*G06T 11/60*  (2006.01)

(52) U.S. Cl.
CPC .......... *G06T 7/0012* (2013.01); *A61B 3/0025* (2013.01); *A61B 3/102* (2013.01); *A61B 3/1233* (2013.01); *A61B 3/1241* (2013.01); *G06T 7/11* (2017.01); *G06T 11/60* (2013.01); *G06T 2200/24* (2013.01); *G06T 2207/10101* (2013.01); *G06T 2207/10121* (2013.01); *G06T 2207/30041* (2013.01)

(58) Field of Classification Search
None
See application file for complete search history.

(56) References Cited

U.S. PATENT DOCUMENTS

| | | |
|---|---|---|
| 2015/0029464 A1 | 1/2015 | Jayasundera |
| 2015/0366452 A1 | 12/2015 | Iwase |
| 2018/0020909 A1* | 1/2018 | Jia .......................... A61B 3/102 351/206 |

OTHER PUBLICATIONS

Feucht et al.; "Multimodal imaging in acute retinal ischemia: spectral domain OCT, OCT-angiography and fundus autofluorescence;" Sep. 18, 2018; Int J Ophthalmol vol. 11(9): pp. 1521-1527. (Year: 2018).*

(Continued)

*Primary Examiner* — Peter Hoang
(74) *Attorney, Agent, or Firm* — FOLEY & LARDNER LLP

(57) ABSTRACT

A non perfusion area is detected from a fundus image. A fundus image is acquired, a first non perfusion area in a first region of the fundus is extracted from the fundus image, and a second non perfusion area in a second region of the fundus is extracted from the fundus image.

7 Claims, 16 Drawing Sheets

(56) References Cited

OTHER PUBLICATIONS

Croft, et al., "Precise Montaging and Metric Quantification of Retinal Surface Area From Ultra-Widefield Fundus Photography and Fluorescein Angiography", Ophthalmic Surgery, Laser and Imaging Retina, vol. 45, No. 4, Jul. 31, 2014, pp. 312-317.

Sim, et al., "Patterns of Peripheral Retinal and Central Macula Ischemia in Diabetic Retinopathy as Evaluated by Ultra-widefield Fluorescein Angiography", American Journal of Ophthalmology, vol. 158, No. 1, Jul. 31, 2014, pp. 144-153.

Singer, et al., "Targeted photocoagulation of peripheral ischemia to treat rebound edema", Clinical Ophthalmology, vol. 9, Feb. 13, 2015, pp. 337-341.

Jia, et al., "Quantitative optical coherence tomography angiography of vascular abnormalities in the living human eye", Proceedings of the National Academy of Sciences of the United States of America, vol. 112, No. 18, May 5, 2015, pp. E2395-E2402.

Japanese Office Action issued in Japanese Patent Application No. 2023-065918 dated Nov. 21, 2023 (8 pages).

Japanese Office Action issued in Japanese Patent Application No. 2023-065918 dated May 28, 2024, with English Translation (5 pages).

\* cited by examiner

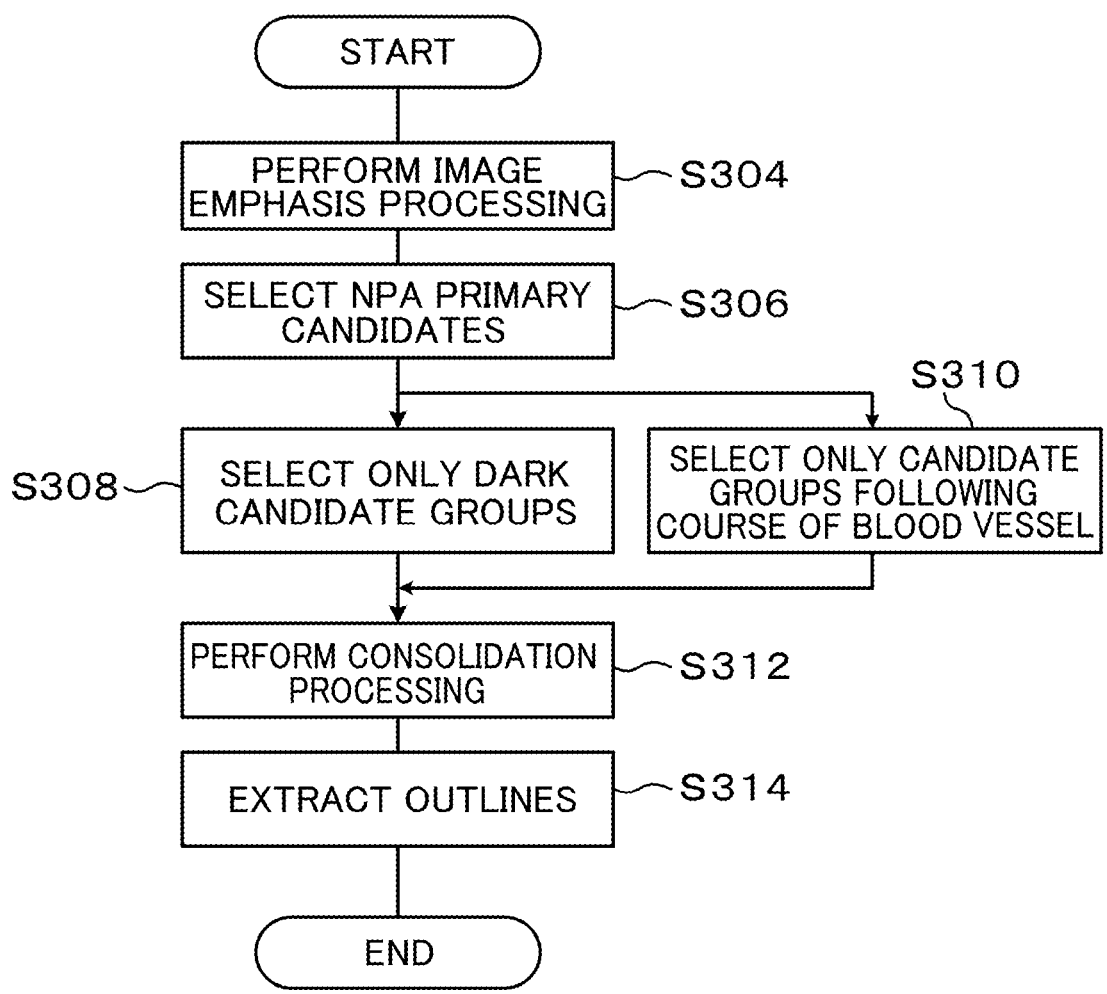

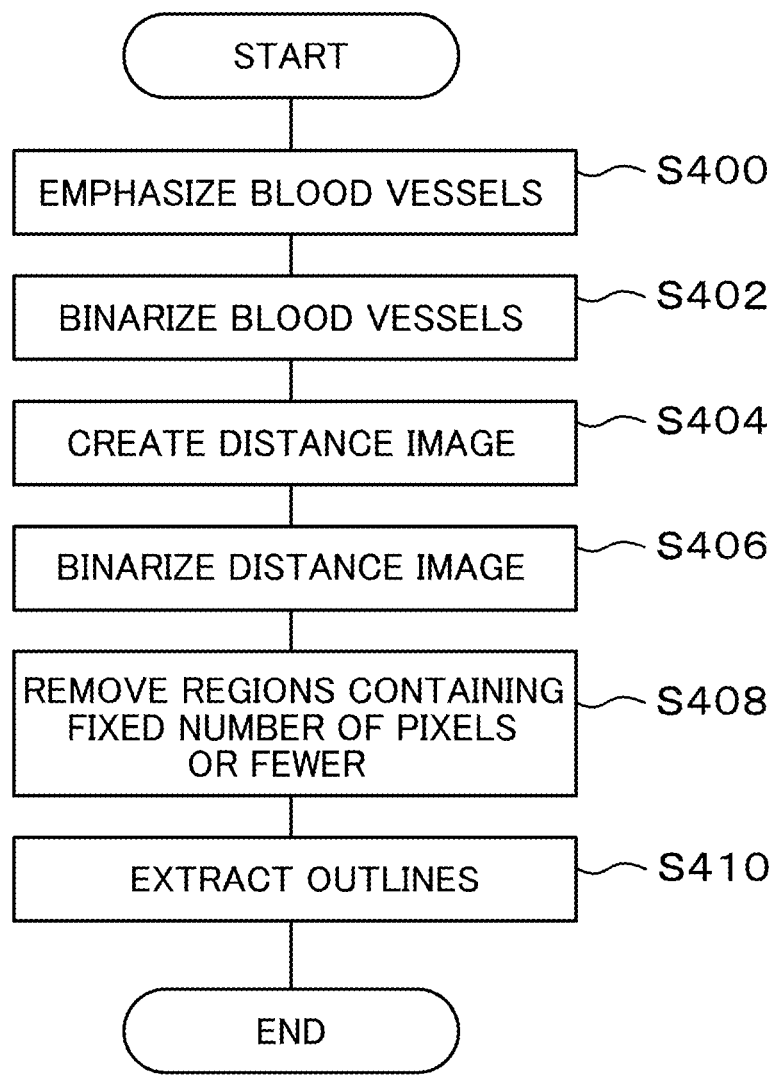

IMAGE PROCESSING METHOD, IMAGE DISPLAY METHOD, IMAGE PROCESSING DEVICE, IMAGE DISPLAY DEVICE, IMAGE PROCESSING PROGRAM, AND IMAGE DISPLAY PROGRAM

CROSS-REFERENCE TO RELATED APPLICATION

This application is a National Stage of International Application No. PCT/JP2018/048578, filed Dec. 28, 2018, the disclosure of which is incorporated herein by reference in its entirety.

BACKGROUND

Technical Field

The technology disclosed herein relates to an image processing method, an image display method, an image processing device, an image display device, an image processing program, and an image display program.

US Patent Application Publication No. 2015/0366452 discloses analysis of a tomographic image of a fundus to extract a region where an abnormality has developed. The ability to confirm an abnormality by analyzing a fundus image is desirable.

SUMMARY OF INVENTION

A first aspect of technology disclosed herein is an image processing method including: a step of acquiring a fundus image; a step of extracting a first non perfusion area in a first region of a fundus from the fundus image; and a step of extracting a second non perfusion area in a second region of the fundus from the fundus image.

A second aspect of technology disclosed herein is an image display method including: a step of acquiring a fundus image and information relating to a first non perfusion area in a first region of a fundus extracted from the fundus image, and a second non perfusion area in a second region of the fundus; and a step of displaying at least one out of the first non perfusion area or the second non perfusion area superimposed on the fundus image.

A third aspect of technology disclosed herein is an image processing program to cause a computer to execute the image processing method of the first aspect.

A fourth aspect of technology disclosed herein is an image processing program to cause a computer to execute the image display method of the second aspect.

A fifth aspect of technology disclosed herein is an image processing device including: a fundus image acquisition section configured to acquire a fundus image; a first non perfusion area extraction section configured to extract from the fundus image a first non perfusion area in a first region of a fundus; and a second non perfusion area extraction section configured to extract from the fundus image a second non perfusion area in a second region of the fundus.

A sixth aspect of technology disclosed herein is an image display device including; an acquisition section configured to acquire a fundus image, information relating to a first non perfusion area in a first region of a fundus extracted from the fundus image, and information relating to a second non perfusion area in a second region of the fundus; and a display section configured to display at least one out of the first non perfusion area or the second non perfusion area superimposed on the fundus image.

BRIEF DESCRIPTION OF DRAWINGS

FIG. 9 is a flowchart illustrating a flow of processing to detect non perfusion areas at a fundus posterior pole portion according to an exemplary embodiment.

FIG. 10 are explanatory diagrams illustrating processing to detect non perfusion areas at a fundus posterior pole portion according to an exemplary embodiment.

FIG. 11 is a flowchart illustrating a flow of processing to detect non perfusion areas at a fundus peripheral portion according to an exemplary embodiment.

DESCRIPTION OF EMBODIMENTS

Detailed explanation follows regarding an exemplary embodiment of the technology disclosed herein, with reference to the drawings.

Figure 1:
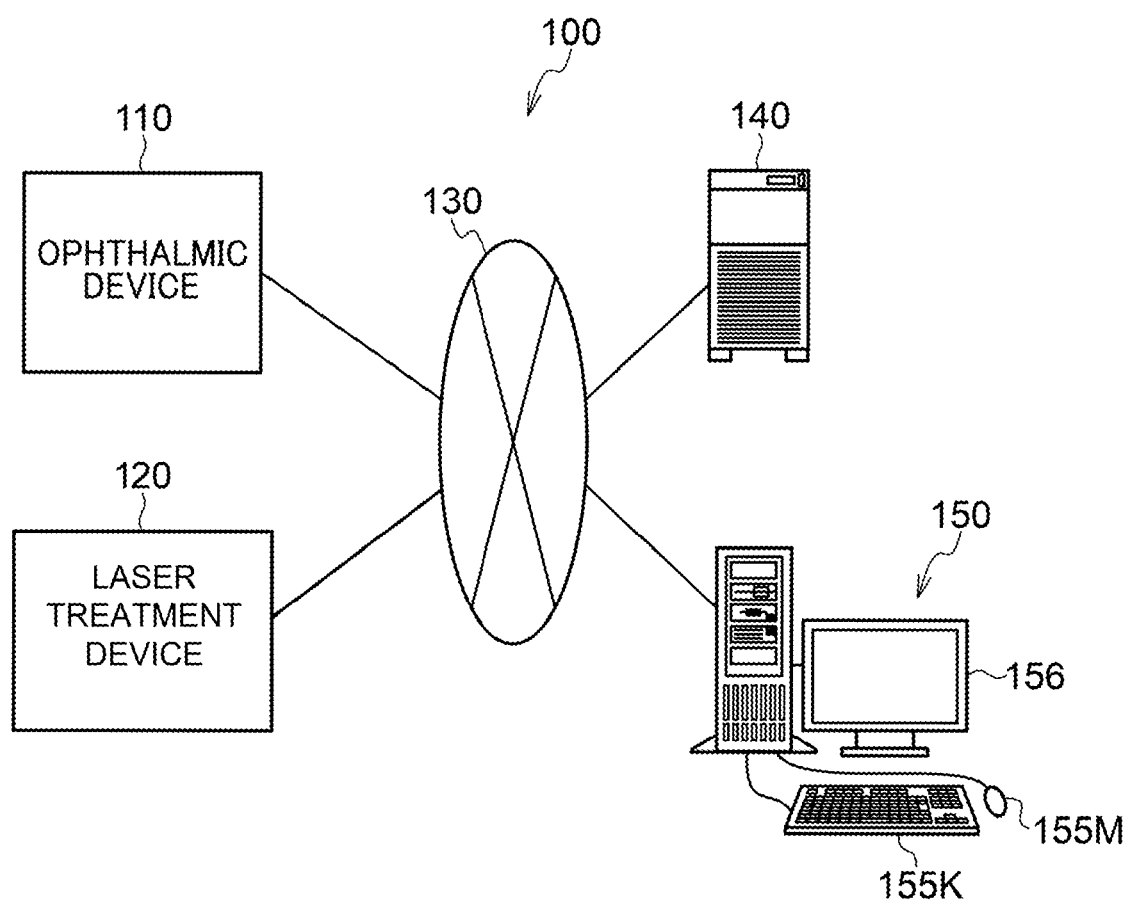
FIG. 1 is a block diagram illustrating an ophthalmic system according to an exemplary embodiment.

Configuration of an ophthalmic system 100 will now be explained with reference to FIG. 1. As illustrated in FIG. 1, the ophthalmic system 100 includes an ophthalmic device 110, a laser treatment device 120, a management server device (referred to hereafter as "management server") 140, and an image display device (referred to hereafter as "image viewer") 150.

The ophthalmic device 110 acquires fundus images and tomographic images. The laser treatment device 120 is a device to support treatment of pathological lesions in an examined eye 12 of a patient. An example of the laser treatment device 120 is a medical apparatus used to suppress progression of a pathological lesion on the optical fundus of a patient, such as a laser photocoagulator that illuminates laser light to cause photocoagulation of the illuminated site. The laser treatment device 120 transmits information relating to treatment performed on the examined eye 12 to the management server 140. For example, when a particular site on the retina of the examined eye 12 is treated, the position of this particular site, the treatment time, and the treatment method are transmitted to the management server 140 as treatment information.

The management server 140 stores plural fundus images obtained by imaging the fundi of plural patients using the ophthalmic device 110, and stores these in association with patient IDs. The management server 140 also detects non perfusion areas (NPAs) in a specified fundus image. The image viewer 150 displays images corresponding to the results of analysis of the fundus images by the management server 140, such as estimated non perfusion areas (NPAs).

The non perfusion areas (NPAs) referred to herein are regions of the ftindus where there is no, or very little, blood flow due to occlusions of the retinal capillary bed, for example. They may also correspond to regions where retinal ischemia has occurred due to perfusion injury.

The ophthalmic device 110, the laser treatment device 120, the management server 140, and the image viewer 150 are coupled together over a network 160.

Although, as described above, the ophthalmic system 100 illustrated in FIG. 1 includes the laser treatment device 120, the technology disclosed herein is not limited thereto. For example, the laser treatment device 120 of the ophthalmic system 100 may be swapped for a measurement instrument such as a field of view measurement instrument for measuring the visual field of a patient, or an eye axial length measurement instrument for measuring the eye axial length, this being the length of the examined eye 12 along an eye axial direction. Moreover, such additional measurement instruments may also be connected over the network 130.

The management server 140 is an example of an "image processing device" of technology disclosed herein. The image viewer 150 is an example of an "image display device" of technology disclosed herein.

For ease of explanation, hereinafter "scanning laser ophthalmoscope" will be abbreviated to SLO, and "optical coherence tomography" will be abbreviated to OCT.

Figure 2:
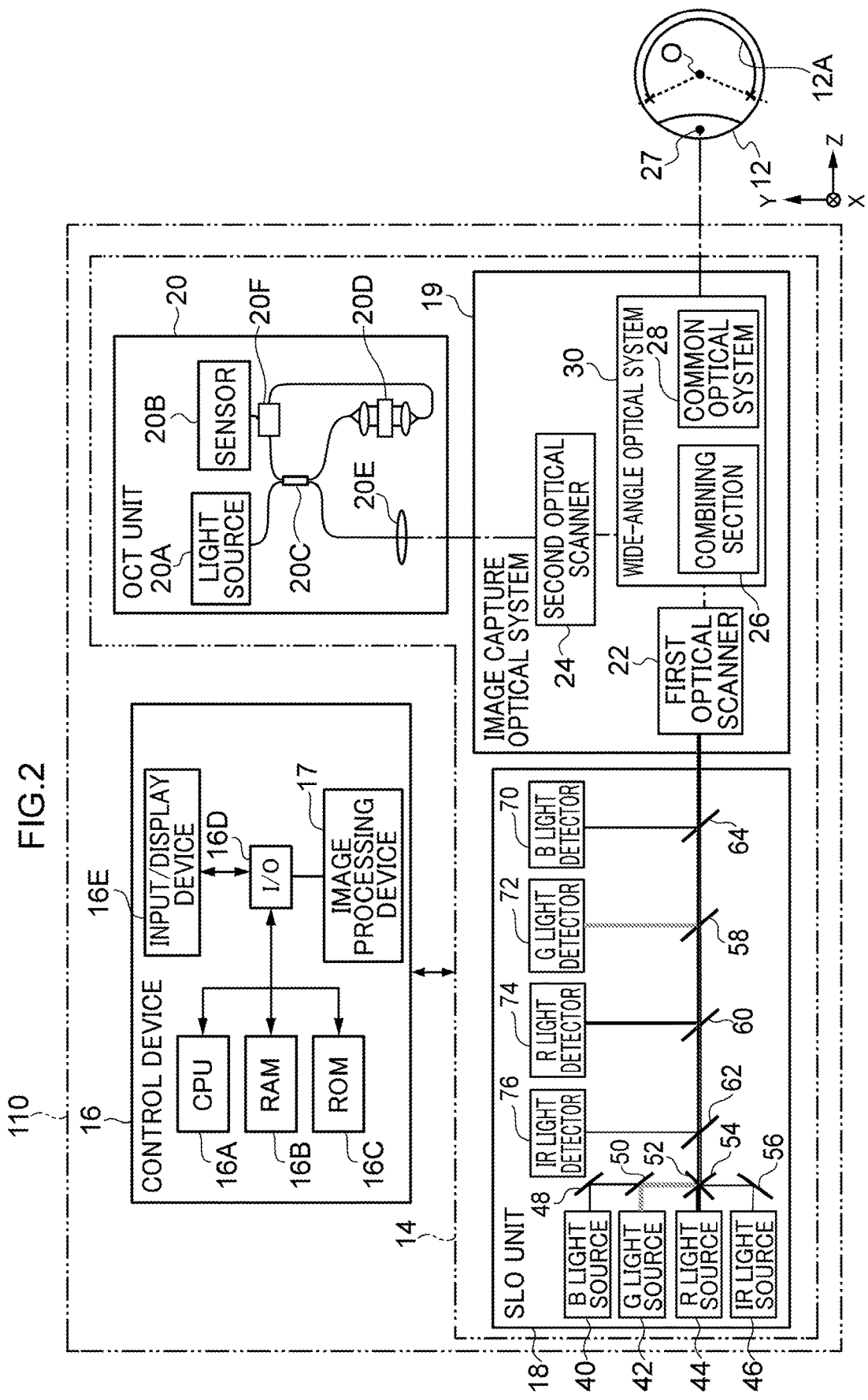
FIG. 2 is a schematic configuration diagram illustrating an overall configuration of an ophthalmic device according to an exemplary embodiment.

Explanation follows regarding configuration of the ophthalmic device 110, with reference to FIG. 2.

In cases in which the ophthalmic device 110 is installed on a horizontal plane with a horizontal direction taken as an X direction, a direction perpendicular to the horizontal plane is taken as a Y direction, and a direction connecting the center of the pupil at the anterior segment of the examined eye 12 and the center of the eyeball is taken as a Z direction. The X direction, the Y direction, and the Z direction are thus mutually orthogonal directions.

The ophthalmic device 110 includes an imaging device 14 and a control device 16. The imaging device 14 is provided with an SLO unit 18 and an OCT unit 20, and acquires a fundus image of the fundus of the examined eye 12. Two-dimensional fundus images that have been acquired by the SLO unit 18 are referred to hereafter as SLO images. Tomographic images, face-on images (en-face images) and the like of the retina created based on OCT data acquired by the OCT unit 20 are referred to hereafter as OCT images.

The control device 16 includes a computer provided with a Central Processing Unit (CPU) 16A, Random Access Memory (RAM) 16B, Read-Only Memory (ROM) 16C, and an input/output (I/O) port 16D.

The control device 16 is provided with an input/display device 16E coupled to the CPU 16A through the I/O port 16D. The input/display device 16E includes a graphical user interface to display images of the examined eye 12 and to receive various instructions from a user. An example of the graphical user interface is a touch panel display.

The control device 16 is provided with an image processing device 17 coupled to the I/O port 16D. The image processing device 17 generates images of the examined eye 12 based on data acquired by the imaging device 14. Note that the control device 16 is coupled to the network 130 through a communication interface, not illustrated in the drawings.

Although the control device 16 of the ophthalmic device 110 is provided with the input/display device 16E as illustrated in FIG. 2, the technology disclosed herein is not limited thereto. For example, a configuration may adopted in which the control device 16 of the ophthalmic device 110 is not provided with the input/display device 16E, and instead a separate input/display device is provided that is physically independent of the ophthalmic device 110. In such cases, the display device is provided with an image processing processor unit that operates under the control of a display control section 204 of the CPU 16A in the control device 16. Such an image processing processor unit may display SLO images and the like based on an image signal output in response to an instruction from the display control section 204.

The imaging device 14 operates under the control of an image capture control section 202 of the control device 16. The imaging device 14 includes the SLO unit 18, an image capture optical system 19, and the OCT unit 20. The image capture optical system 19 includes a first optical scanner 22, a second optical scanner 24, and a wide-angle optical system 30.

The first optical scanner 22 scans light emitted from the SLO unit 18 two dimensionally in the X direction and the Y direction. The second optical scanner 24 scans light emitted from the OCT unit 20 two dimensionally in the X direction and the Y direction. As long as the first optical scanner 22 and the second optical scanner 24 are optical elements capable of polarizing light beams, they may be configured by any out of, for example, polygon mirrors, mirror galvanometers, or the like. A combination thereof may also be employed.

The wide-angle optical system 30 includes an objective optical system (not illustrated in FIG. 2) provided with a common optical system 28, and a combining section 26 that combines light from the SLO unit 18 with light from the OCT unit 20.

The objective optical system of the common optical system 28 may be a reflection optical system employing a concave mirror such as an elliptical mirror, a diffraction optical system employing a wide-angle lens, or may be a reflection-diffraction optical system employing a combination of a concave mirror and a lens. Employing a wide-angle optical system that utilizes an elliptical mirror, wide-angle lens, or the like enables imaging to be performed of not only a central portion of the fundus (fundus posterior pole portion), but also of the retina at a peripheral portion of the fundus.

For a system including an elliptical mirror, a configuration may be adopted that utilizes an elliptical mirror system as disclosed in International Publication (WO) Nos. 2016/

103484 or 2016/103489. The disclosures of WO Nos. 2016/103484 and 2016/103489 are incorporated in their entirety by reference herein.

Observation of the fundus over a wide field of view (FOV) 12A is implemented by employing the wide-angle optical system 30. The FOV 12A refers to a range capable of being imaged by the imaging device 14. The FOV 12A may be expressed as a view angle. In the present exemplary embodiment the viewing angle may be defined in terms of an internal illumination angle and an external illumination angle. The external illumination angle is the angle of illumination by a light beam shone from the ophthalmic device 110 toward the examined eye 12, and is an angle of illumination defined with respect to a pupil 27. The internal illumination angle is the angle of illumination of a light beam shone onto the fundus F, and is an angle of illumination defined with respect to an eyeball center O. A correspondence relationship exists between the external illumination angle and the internal illumination angle. For example, an external illumination angle of 120° is equivalent to an internal illumination angle of approximately 160°. The internal illumination angle in the present exemplary embodiment is 200°.

SLO fundus images obtained by imaging over a view angle having an internal illumination angle of 160° or greater are referred to as UWF-SLO fundus images. UWF is an abbreviation of ultra-wide field.

An SLO system is realized by the control device 16, the SLO unit 18, and the image capture optical system 19 as illustrated in FIG. 2. The SLO system is provided with the wide-angle optical system 30, enabling fundus imaging over the wide FOV 12A.

The SLO unit 18 is provided with a blue (B) light source 40, a green (G) light source 42, a red (R) light source 44, an infrared (for example near infrared) (IR) light source 46, and optical systems 48, 50, 52, 54, 56 to guide the light from the light sources 40, 42, 44, 46 onto a single optical path using transmission or reflection. The optical systems 48, 50, 56 are configured by mirrors, and the optical systems 52, 54 are configured by beam splitters. B light is reflected by the optical system 48, is transmitted through the optical system 50, and is reflected by the optical system 54. G light is reflected by the optical systems 50, 54, R light is transmitted through the optical systems 52, 54, and IR light is reflected by the optical systems 52, 56. The respective colors of light are thereby guided onto a single optical path.

The SLO unit 18 is configured so as to be capable of switching between the light source or the combination of light sources employed when emitting laser light of different wavelengths, such as in a mode in which R light and G light are emitted, a mode in which infrared light is emitted, etc. Although the example in FIG. 2 includes three light sources, i.e. the G light source 42, the R light source 44, and the IR light source 46, the technology disclosed herein is not limited thereto. For example, the SLO unit 18 may, furthermore, also include a blue (B) light source or a white light source, in a configuration in which light is emitted according to various modes, such as a mode in which G light, R light, and B light are emitted or a mode in which white light is emitted alone.

Light introduced to the image capture optical system 19 from the SLO unit 18 is scanned in the X direction and the Y direction by the first optical scanner 22. The scanning light passes through the wide-angle optical system 30 and the pupil 27 and is shone onto the fundus. Reflected light that has been reflected by the fundus passes through the wide-angle optical system 30 and the first optical scanner 22 and is introduced into the SLO unit 18.

The SLO unit 18 is provided with a beam splitter 64 and a beam splitter 58. From out of the light coming from the posterior eye portion (fundus) of the examined eye 12, the B light therein is reflected by the beam splitter 64 and light other than the B light is transmitted through the beam splitter 64. From out of the light transmitted through the beam splitter 64, the G light therein is reflected by the beam splitter 58 and light other than the G light is transmitted through the beam splitter 58. The SLO unit 18 is further provided with a beam splitter 60 that, from out of the light transmitted through the beam splitter 58, reflects R light therein and transmits light other than the R light. The SLO unit 18 is further provided with a beam splitter 62 that reflects IR light from out of the light transmitted through the beam splitter 60. The SLO unit 18 is further provided with a B light detector 70 to detect the B light reflected by the beam splitter 64, a G light detector 72 to detect the G light reflected by the beam splitter 58, an R light detector 74 to detect the R light reflected by the beam splitter 60, and an IR light detector 76 to detect the IR light reflected by the beam splitter 62.

Of the light that has passed through the wide-angle optical system 30 and the first optical scanner 22 and been introduced into the SLO unit 18 (i.e. reflected light that has been reflected by the fundus), the B light therein is reflected by the beam splitter 64 and photo-detected by the B light detector 70, and the G light therein is reflected by the beam splitter 58 and photo-detected by the G light detector 72. R light of this introduced light is transmitted through the beam splitter 58, reflected by the beam splitter 60, and photo-detected by the R light detector 74. IR light of this introduced light is transmitted through the beam splitters 58, 60, reflected by the beam splitter 62, and photo-detected by the IR light detector 76. The image processing device 17 that operates under the control of the CPU 16A employs detection signals from the B light detector 70, the G light detector 72, the R light detector 74, and the IR light detector 76 to generate UWF-SLO images.

These UWF-SLO images include a UWF-SLO image (G fundus image) obtained by imaging the fundus in green, and a UWF-SLO image (R fundus image) obtained by imaging the fundus in red. The UWF-SLO images further include a UWF-SLO image (B fundus image) obtained by imaging the fundus in blue, and a UWF-SLO image (IR fundus image) obtained by imaging the fundus in IR.

The control device 16 may control the light sources 40, 42, 44 so as to emit light at the same time as each other. The G fundus image, the R fundus image, and the B fundus image may be obtained at mutually corresponding positions by imaging the fundus of the examined eye 12 using B light, G light, and R light at the same time. An RGB color fundus image may be obtained from the G fundus image, the R fundus image, and the B fundus image. The control device 16 may also control the light sources 42, 44 so as to emit light at the same time as each other. The G fundus image and the R fundus image are obtained at mutually corresponding positions by imaging the fundus of the examined eye 12 using G light and R light at the same time in this manner. An RG color fundus image may be obtained from the G fundus image and the R fundus image.

The UWF-SLO images may further include a UWF-SLO fluoroscopy image obtained by fluoroscopy using a contrast agent.

Image data for the B fundus image, the G fundus image, the R fundus image, the IR fundus image, the RGB color fundus image, the RG color fundus image, and the UWF-SLO fluoroscopy image are sent from the ophthalmic device 110 to the management server 140 through a non-illustrated communication IF.

An OCT system is realized by the control device 16, the OCT unit 20, and the image capture optical system 19 illustrated in FIG. 2. The OCT system is provided with the wide-angle optical system 30. This enables fundus imaging to be performed over the wide FOV 12A similarly to when imaging the SLO fundus images as described above. The OCT unit 20 includes a light source 20A, a sensor (detector) 20B, a first light coupler 20C, a reference optical system 20D, a collimator lens 20E, and a second light coupler 20F.

Light emitted from the light source 20A is split by the first light coupler 20C. After one part of the split light has been collimated by the collimator lens 20E into parallel light, to serve as measurement light, the parallel light is introduced into the image capture optical system 19. The measurement light is scanned in the X direction and the Y direction by the second optical scanner 24. The scanned light is shone onto the fundus through the wide-angle optical system 30 and the pupil 27. Measurement light that has been reflected by the fundus passes through the wide-angle optical system 30 and the second optical scanner 24 so as to be introduced into the OCT unit 20. The measurement light then passes through the collimator lens 20E and the first light coupler 20C before being introduced to the second light coupler 20F.

The remainder of the light emitted from the light source 20A and split by the first light coupler 20C is introduced into the reference optical system 20D as reference light, and is introduced to the second light coupler 20F through the reference optical system 20D.

The respective lights introduced to the second light coupler 20F, namely the measurement light reflected by the fundus and the reference light, interfere with each other in the second light coupler 20F so as to generate interference light. The interference light is photo-detected by the sensor 20B. The image processing device 17 operating under the control of an image processing control section 206 generates OCT images, such as tomographic images and en-face images, based on OCT data detected by the sensor 20B.

Note that the OCT unit 20 is able to obtain OCT data for OCT images, which are tomographic images of the examined eye 12. Examples of OCT images include: a one-dimensional OCT image that is an A-scan image obtained by performing what is referred to as an A-scan using the ophthalmic device 110; a two-dimensional OCT image that is a B-scan image obtained by performing what is referred to as a B-scan using the ophthalmic device 110; and a three-dimensional OCT image that is a C-scan image obtained by performing what is referred to as a C-scan using the ophthalmic device 110.

OCT fundus images obtained by imaging over a view angle having an internal illumination angle of 160° or greater are referred to as UWF-OCT images.

Image data of the UWF-OCT images is sent from the ophthalmic device 110 to the management server 140 through the non-illustrated communication IF and stored in a storage device 254.

Note that although in the present exemplary embodiment an example is given in which the light source 20A is a swept-source OCT (SS-OCT), the light source 20A may be from various OCT systems, such as from a spectral-domain OCT (SD-OCT) or a time-domain OCT (TD-OCT) system.

Figure 3:
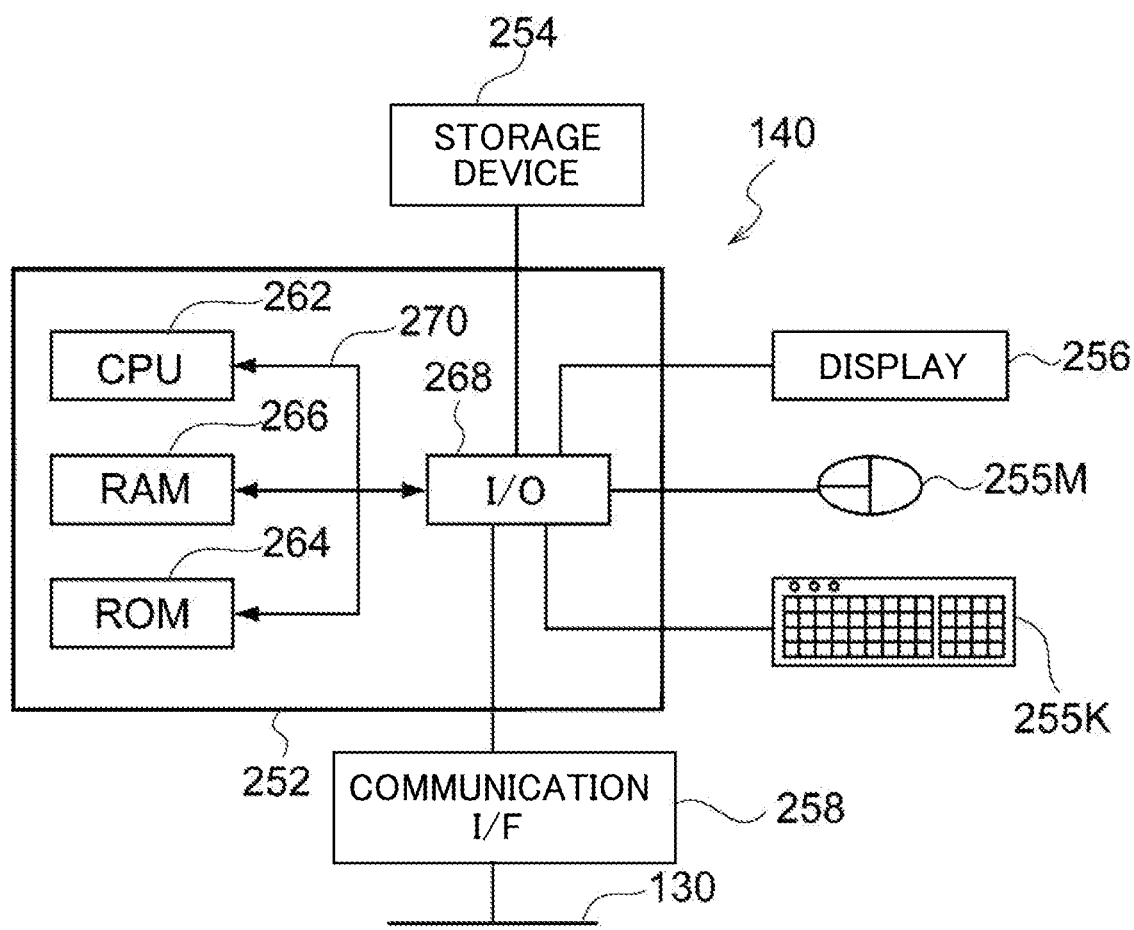
FIG. 3 is a block diagram illustrating a configuration of an electrical system of a management server according to an exemplary embodiment.

Explanation follows regarding a configuration of an electrical system of the management server 140, with reference to FIG. 3. As illustrated in FIG. 3, the management server 140 is provided with a computer unit 252. The computer unit 252 includes a CPU 262, RAM 266, ROM 264, and an input/output (I/O) port 268. A storage device 254, a display 256, a mouse 255M, a keyboard 255K, and a communication interface (I/F) 258 are coupled to the input/output (I/O) port 268. The storage device 254 is, for example, configured by non-volatile memory. The input/output (I/O) port 268 is coupled to the network 130 through the communication interface (I/F) 258. The management server 140 is thus capable of communicating with the ophthalmic device 110, the laser treatment device 120, and the image viewer 150.

The management server 140 stores various data received from the ophthalmic device 110 and the laser treatment device 120 in the storage device 254.

Figure 4:
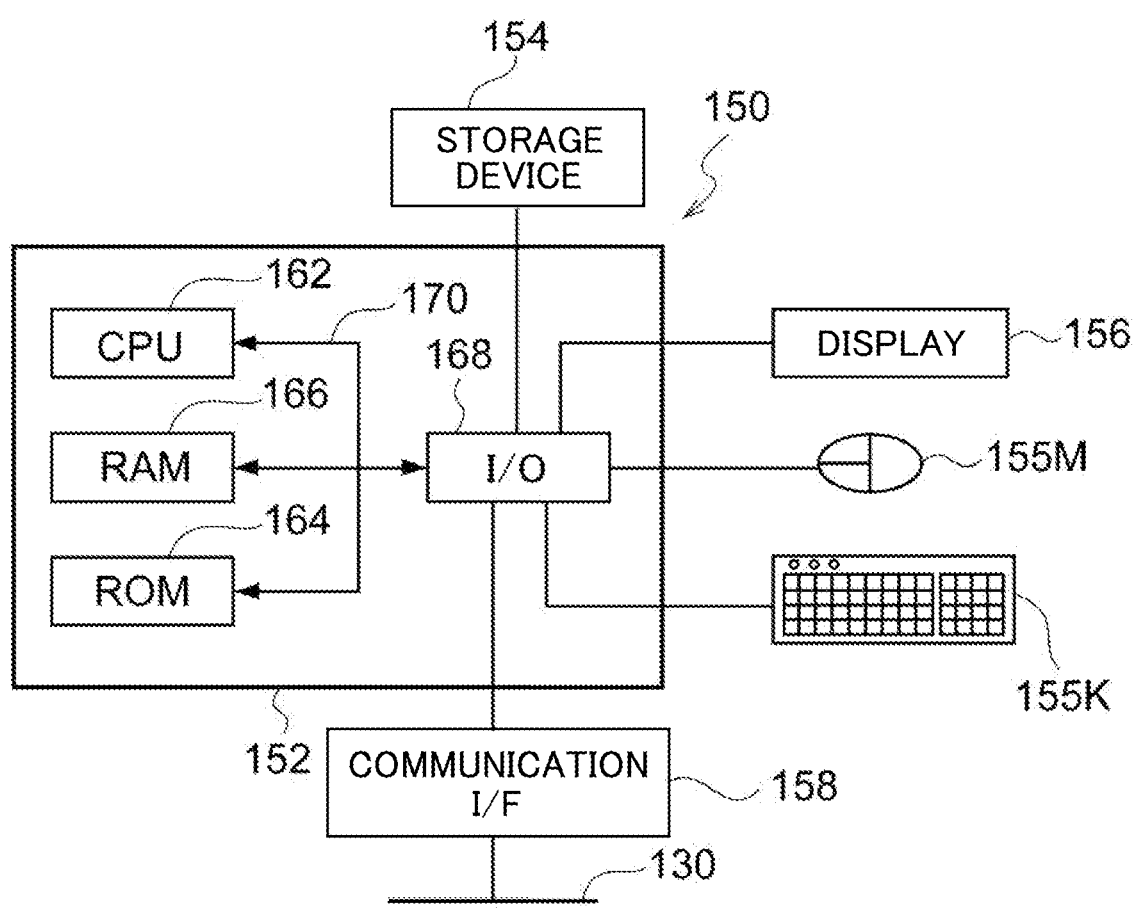
FIG. 4 is a block diagram illustrating a configuration of an electrical system of an image viewer according to an exemplary embodiment.

Explanation follows regarding a configuration of an electrical system of the image viewer 150, with reference to FIG. 4. As illustrated in FIG. 4, the image viewer 150 is provided with a computer unit 152. The computer unit 152 includes a CPU 162, RAM 166, ROM 164, and an input/output (I/O) port 168. A storage device 154, a display 156, a mouse 155M, a keyboard 155K, and a communication interface (I/F) 158 are coupled to the input/output (I/O) port 168. The storage device 154 is, for example, configured by non-volatile memory. The input/output (I/O) port 168 is coupled to the network 130 through the communication interface (I/F) 158. The image viewer 150 is thus capable of communicating with the ophthalmic device 110 and the management server 140.

Figure 5:
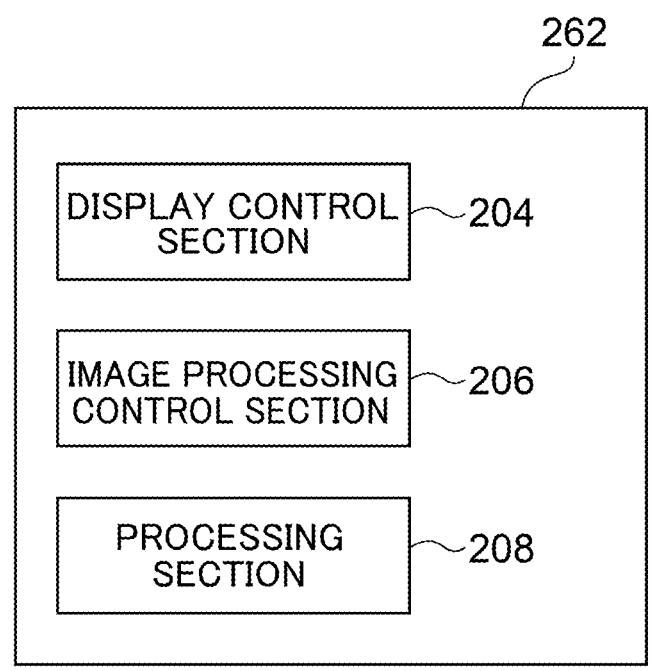
FIG. 5 is a block diagram illustrating functionality of a CPU of a management server according to an exemplary embodiment.

Explanation follows regarding various functions implemented by the CPU 262 of the management server 140 executing an image processing program, with reference to FIG. 5. As illustrated in FIG. 5, the image processing program includes a display control function, an image processing control function, and a processing function. The CPU 262 functions as the display control section 204, the image processing control section 206, and a processing section 208 illustrated in FIG. 5 by the CPU 262 executing the image processing program that includes these functions.

Figure 6:
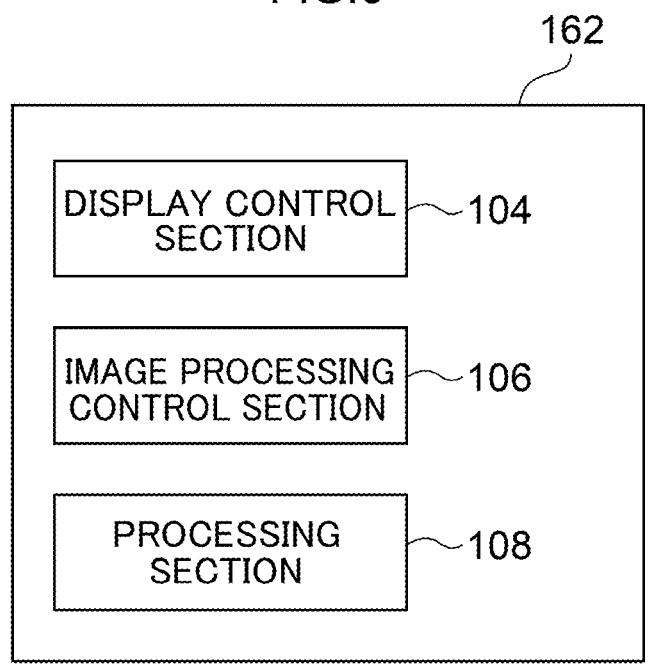
FIG. 6 is a block diagram illustrating functionality of a CPU of an image viewer according to an exemplary embodiment.

Next, explanation follows regarding various functions implemented by the CPU 162 of the image viewer 150 executing the image processing program, with reference to FIG. 6. As illustrated in FIG. 6, the image processing program includes a display control function, an image processing control function, and a processing function. The CPU 162 functions as a display control section 104, an image processing control section 106, and a processing section 108 illustrated in FIG. 6 by the CPU 162 executing the image processing program that includes these functions.

The image processing control section 206 is an example of a "fundus image acquisition section", a "first non perfusion area extraction section", and a "second non perfusion area extraction section" of technology disclosed herein.

The image processing control section 106 is an example of an "acquisition section" of technology disclosed herein, and the display 156 is an example of a "display section" of technology disclosed herein.

Figure 7:
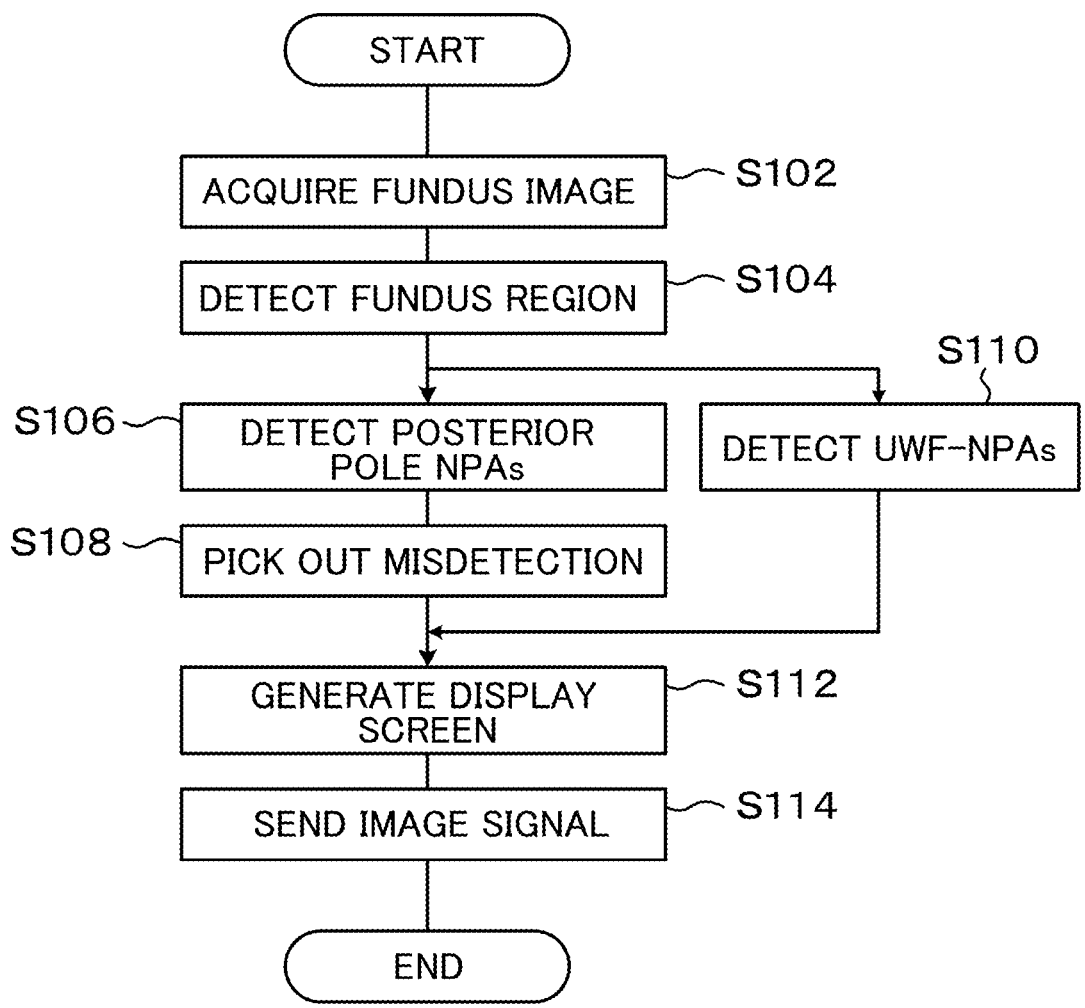
FIG. 7 is a flowchart for an image processing program executed by a management server according to an exemplary embodiment.

Next, detailed explanation follows regarding image processing by the management server 140, with reference to FIG. 7. The image processing illustrated in the flowchart of FIG. 7 is implemented by the CPU 262 of the management server 140 executing the image processing program.

The image processing illustrated in FIG. 7 is an example of an image processing method of technology disclosed herein. Moreover, the display processing to display images obtained by the image processing illustrated in FIG. 7 is an example of an image display method of technology disclosed herein.

Note that various data (for example, image data of UWF-SLO images, and image data of UWF-OCT images) obtained by executing processing such as UWF-SLO image processing and UWF-OCT image processing is saved in the storage device 254.

In the present exemplary embodiment, an example of a UWF-SLO image employed in NPA detection is a UWF-SLO image obtained by fluorescein angiography (FA). Such images are referred to hereafter as FA images. Capillaries of the retina are imaged at high resolution in FA images, and so FA images are well-suited to non perfusion area detection. The image data of such FA images is sent from the ophthalmic device 110 to the management server 140 via a non-illustrated communication IF, and is stored in the storage device 254.

Note that UWF-SLO images obtained by imaging using indocyanine green (ICG) as a contrast agent (obtained by indocyanine green angiography) (hereafter referred to as IA images) may also be employed. The blood vessels of the fundus appear white in FA images and IA images.

First, at step S102 in FIG. 7, the image processing control section 206 function realized by the management server 140 acquires the FA image from the storage device 254. Note that the FA images are imaged using the ophthalmic device 110 and then stored in the storage device 254.

Figure 8:
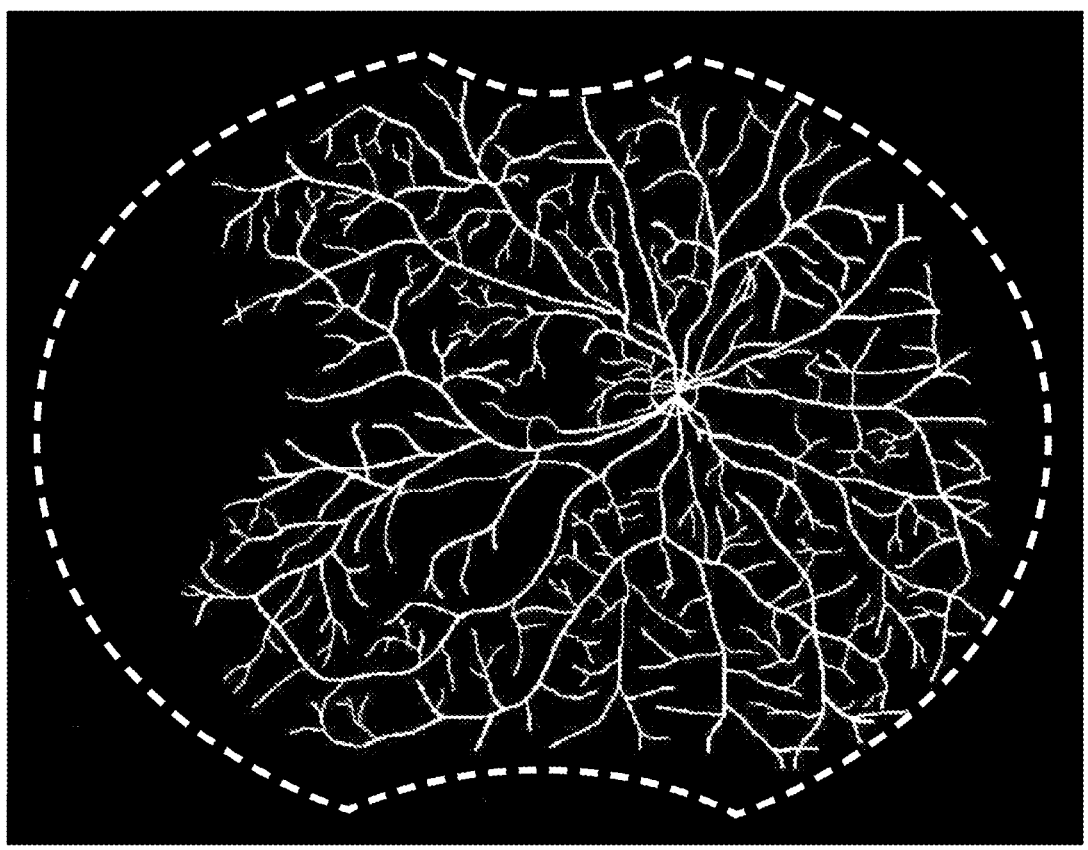
FIG. 8 is a diagram illustrating a fundus region in a fundus image according to an exemplary embodiment.

Next, at step S104, the image processing control section 206 detects the fundus region of the examined eye 12 in the acquired FA image. At step S104, the fundus region of the examined eye 12 is detected by removing sites peripheral to the examined eye 12, such as the eyelashes and eyelids of the patient, and regions where elements configuring the ophthalmic device 110 intrude into the image, and extracting the remaining region as the fundus region. This processing to extract the fundus region may be implemented by image processing configured by a combination of known processing, such as binarization processing and morphological processing. FIG. 8 illustrates an image of an extracted fundus region after the processing of step S104 has been performed. The broken line in FIG. 8 serves to schematically illustrate the edge of the fundus region, and no such broken line is actually present in the image after performing the processing of step S104.

Next the image processing control section 206 detects non perfusion areas (NPAs) in the detected fundus region.

Since, for example, there are differences between the distribution of retinal blood vessels at the fundus posterior pole portion and in a peripheral portion of the fundus peripheral to the fundus posterior pole portion, in the present exemplary embodiment image processing is preferably executed according to the site within the fundus region of the examined eye 12. Accordingly, in the present exemplary embodiment, image processing is performed to visually classify the non perfusion areas (NPAs) of the fundus region into non perfusion areas (NPAs) at the fundus posterior pole portion (hereafter referred to as posterior pole portion NPAs) and non perfusion areas in the fundus peripheral portion (hereafter referred to as UWF-NPAs). A posterior pole portion NPA is a search target in a fundus region where retinal blood vessels are grouped closely together, and a UWF-NPA is a search target in the fundus peripheral region. Thus in the present example, the FA image is subjected to processing optimized for detection of posterior pole portion NPAs (the processing of FIG. 9 or FIG. 16, described later), and processing optimized for detection of UWF-NPAs (the processing of FIG. 11, described later).

Specifically, at step S106 the image processing control section 206 performs detection for posterior pole portion NPAs in the fundus region of the examined eye 12, and at step S108 the image processing control section 206 performs image processing on the detected posterior pole portion NPAs to pick out any misdetected posterior pole portion NPAs among the detected posterior pole portion NPAs. In addition, the image processing control section 206 performs UWF-NPA image processing at step S110 to detect for UWF-NPAs in the fundus region of the examined eye 12. Note that a misdetected posterior pole portion NPA is a region that has a low likelihood of being an actual posterior pole portion NPA despite having been detected as a posterior pole portion NPA.

The fundus posterior pole portion of the examined eye 12 is an example of a "first region" of technology disclosed herein, and the posterior pole portion NPA is an example of a "first non perfusion area" of technology disclosed herein. Moreover, the fundus peripheral portion, at the periphery of the fundus posterior pole portion of the examined eye 12, is an example of a "second region" of technology disclosed herein, and the UWF-NPA is an example of a "second non perfusion area" of technology disclosed herein. Moreover, a misdetected posterior pole portion NPA, this being a region having a low likelihood of being an actual posterior pole portion NPA, is an example of a "third non perfusion area" of technology disclosed herein.

Note that either out of step S106 followed by step S108, or step S110, may be executed first, or execution thereof may be simultaneous. After the processing of both step S106 followed by step S108 and step S110 has been completed, the image processing control section 206 executes image processing at step S112 to generate a display screen. As will be described in detail later, the display screen thus generated is a display screen of the FA image, with outlines of posterior pole portion NPAs displayed superimposed on the FA image so as to enable the positions of the posterior pole portion NPAs to be easily recognized, and with outlines of UWF-NPAs displayed superimposed on the FA image so as to enable the positions of the UWF-NPA to be easily recognized. At step S114, the processing section 208 sends a display image of the generated display screen to the image viewer 150.

Next, explanation follows regarding image processing for posterior pole portion NPAs, with reference to FIG. 9 and FIGS. 10A-10C.

As illustrated in FIG. 9, at step S304, the image processing control section 206 performs image emphasis processing on the acquired FA image to emphasize the vascular portions thereof. This processing is processing to make the blood vessels, including capillary blood vessels, more prominent in order to estimate posterior pole portion NPAs with good precision.

The image emphasis processing may employ various methods, such as emphasis processing in which an image histogram is subjected to histogram averaging or contrast limited adaptive histogram equalization (CLAHE), or alternatively contrast conversion processing based on gradation conversion, frequency emphasis processing for a particular frequency band employing an unsharp mask or the like, deconvolution processing employing a Weiner filter or the like, morphology processing to emphasize the shape of the vascular portions, or the like. Preferably histogram averaging or adaptive histogram equalization is employed therefor. The blood vessels are emphasized as a result of the image emphasis processing.

Next the image processing control section 206 estimates plural posterior pole portion NPAs from the FA image in which the blood vessels have been emphasized. More specifically, at step S306, the image processing control section 206 selects primary candidates for posterior pole portion NPAs. More specifically, the image processing control section 206 extracts plural pixels of a first darkness or darker from the FA image in which the blood vessels have been emphasized, and selects as primary candidates for the posterior pole portion NPAs a single or plural regions having a surface area of a prescribed surface area or greater of contiguous pixels of the first darkness or darker.

The pixels of the first darkness or darker referred to here are pixels having a pixel value of a first prescribed value or lower. For example, brightness values expressing lightness may be employed as the pixel values. Alternatively, values expressing at least one out of saturation or hue may be employed as the pixel values instead of brightness values, or in addition to brightness values.

Next, the image processing control section 206 executes the image processing of step S308 and step S310.

At step S308, from out of the single or plural primary candidates for posterior pole portion NPAs, the image processing control section 206 selects only dark candidates based on an average value of the respective pixel values in each of the candidate regions. Specifically, the image processing control section 206 calculates an average value of the pixel values in each of the regions corresponding to the single or plural primary candidates for posterior pole portion NPAs, and selects as a dark region a single or plural candidates having a calculated average value smaller than a second prescribed value. The second prescribed value is a prescribed value smaller than the first prescribed value. Namely, only candidates corresponding to dark regions having a darkness that is a second darkness darker than the first darkness, or darker (i.e. candidates having a prescribed average pixel value or less) are extracted from the primary candidates of the first darkness, thus yielding first secondary candidates.

At step S310, the image processing control section 206 narrows down the plural primary candidates for posterior pole portion NPAs to only regions that follow the course of a blood vessel. More specifically, first the image processing control section 206 (1) extracts blood vessels. The blood vessels are extracted based on the pixel values using a method such as morphological processing or binarization. Note that the regions extracted thereby are referred to as vascular regions. Then the image processing control section 206 uses (2) a method such as distance conversion to compute a distance between such vascular regions and the peripheral edges of the single or plural primary candidates for posterior pole portion NPAs, or of respective region groups of candidate groups for posterior pole portion NPAs, and selects regions in which this computed distance is within a fixed range.

The fixed range referred to here is a first range that is larger than a first prescribed distance, but smaller than a second prescribed distance larger than the first prescribed distance (namely, when following blood vessels).

Thus at step S310, from the primary candidates, the image processing control section 206 extracts as second secondary candidates any regions for which the distance to a blood vessel is a first distance or lower. Note that for the second secondary candidates, a region that is a fixed range away from a blood vessel terminal end may be employed as a second secondary candidate.

Either out of step S308 or step S310 may be executed first, or alternatively step S308 and step S310 may be executed simultaneously. The image processing control section 206 executes the image processing illustrated in step S312 after the processing of step S308 and step S310 have been completed.

At step S312, the image processing control section 206 performs consolidation processing to consolidate the first secondary candidates and the second secondary candidates. Specifically, regions corresponding to both a first secondary candidate (the plural dark regions) and a second secondary candidate (the plural regions following blood vessels) are extracted, and these regions are identified as posterior pole portion NPAs.

Figure 10A:
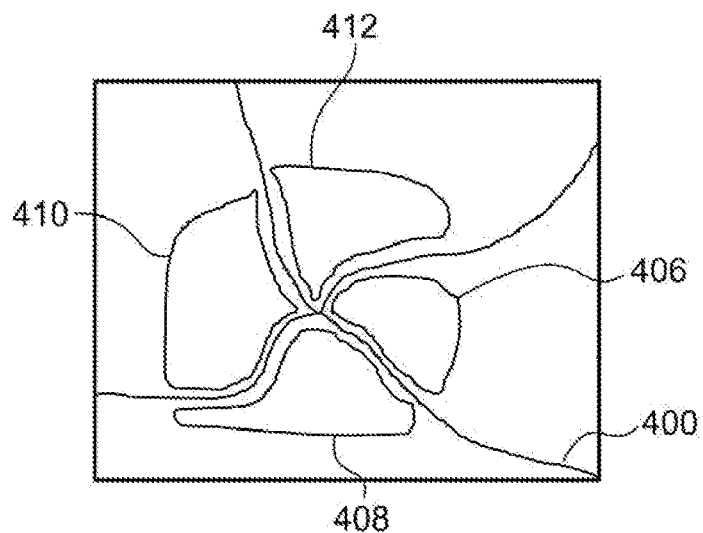
FIG. 10A illustrates a primary candidate.
Figure 10B:
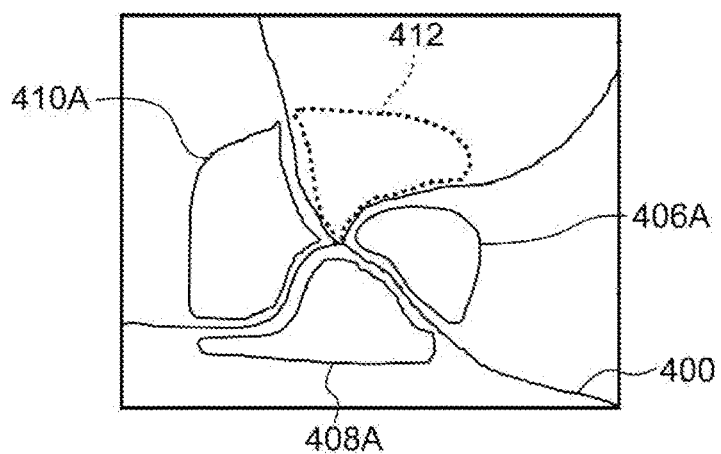
FIG. 10B illustrates exclusion of a primary candidate.
Figure 10C:
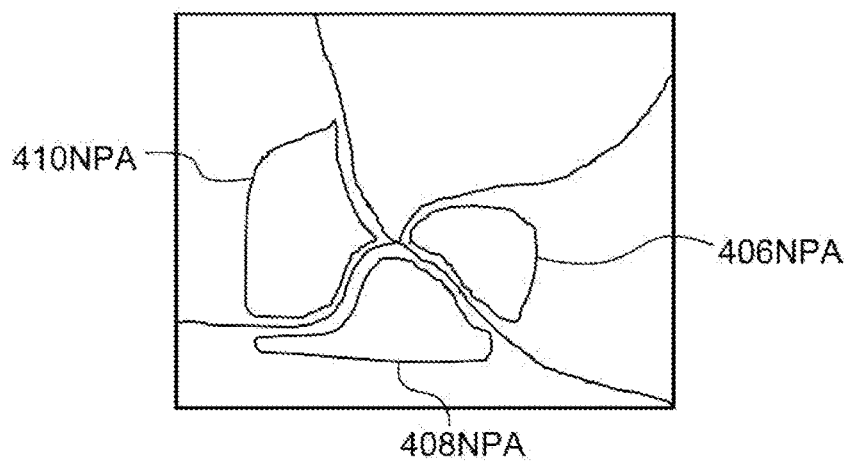
FIG. 10C illustrates identified non perfusion areas at a fundus posterior pole portion.

FIG. 10 are schematic diagrams illustrating part of an FA image in close up in order to illustrate results of the processing of step S306 to step 312 in simplified form. FIG. 10A illustrates blood vessels 400 and four primary candidates 406, 408, 410, 412 for posterior pole portion NPAs following the processing of step S306. For ease of explanation, the blood vessels 400 are illustrated by black lines in FIG. 10. In FIG. 10B, primary candidates 406A, 408A, 410A illustrated by solid lines are examples of primary candidates estimated by the processing of step S308 and step S310. Moreover, in FIG. 10B, the primary candidate 412 illustrated with dotted lines is an example of a primary candidate that has been excluded. In FIG. 10C, estimated candidates 406NPA, 408NPA, 410NPA narrowed down as secondary candidates from the primary candidates that correspond to both the first secondary candidates and the second secondary candidate are illustrated as identified posterior pole portion NPAs.

Next, at step S314 of FIG. 9, the image processing control section 206 extracts the outlines of the posterior pole portion NPAs in the FA image. The outlines of the posterior pole portion NPAs are images to be displayed superimposed on the FA image so as to be allow the positions of the posterior pole portion NPAs on the FA image to be easily recognized. The image processing relating to the posterior pole portion NPAs is performed as described above.

Next, explanation follows regarding processing to pick out misdetection of the posterior pole portion NPAs at step S108 illustrated in FIG. 7.

The regions detected as the posterior pole portion NPAs as described above (step S106) may include regions that do not actually correspond to a posterior pole portion NPA (hereafter referred to as a non-NPAs). Examples of such misdetected non-NPAs include regions corresponding to spots and the like where imaging light does not reach the retina due to the presence of a photocoagulation spot, soft exudate, or cataracts.

At step S108 of FIG. 7, the image processing control section 206 accordingly picks out any misdetected posterior pole portion NPAs present among the posterior pole portion NPAs detected at step S106. More specifically, the following discrimination methods may be employed to discriminate any misdetected posterior pole portion NPAs present among the detected posterior pole portion NPAs.

In a first discrimination method, image processing is performed using an image filter for detecting photocoagulation spots by employing image data of known photocoagulation spots. Posterior pole portion NPAs and photocoagulation spots are discriminated, and if a posterior pole portion NPA is discriminated as being a photocoagulation spot in this discrimination, this posterior pole portion NPA discriminated as being a photocoagulation spot is picked out as a non-NPA. Note that the image filter employed in the first discrimination method is not limited to a filter for detecting photocoagulation spots, and an image filter for detecting regions such as spots where imaging light does not reach the retina due to the presence of a soft exudate or cataract may be employed instead.

In a second discrimination method, posterior pole portion NPAs and photocoagulation spots are discriminated using a machine learning AI trained with image data of known photocoagulation spots. If a posterior pole portion NPA is discriminated as being a photocoagulation spot, this posterior pole portion NPA discriminated as being a photocoagulation spot is picked out as a non-NPA. Note that in the second discrimination method, there is no limitation to a machine learning AI trained using image data of photocoagulation spots, and machine learning training may be performed using image data illustrating regions such as spots where imaging light does not reach the retina due to the presence of a soft exudate or cataract instead.

In a third discrimination method, data representing non-NPAs is acquired from another image handling device, and any non-NPAs among the detected posterior pole portion NPAs are picked out using the acquired data.

For example, in the case of soft exudates, the positions of identified soft exudates may be identified using OCT B-scan images. Any posterior pole portion NPAs at these identified positions are then excluded as being soft exudates. Moreover, in the case of photocoagulation spots, positions where laser illumination has been performed with the laser treatment device 120 may be identified. Any posterior pole portion NPAs at these identified laser-illuminated positions are then excluded as being photocoagulation spots. Data representing non-NPAs from another image handling device as employed in this third discrimination method is an example of data for identifying non-NPAs, but there is no limitation thereto. Any data capable of identifying non-NPAs may be employed as such data.

Detected posterior pole portion NPAs that are misdetected posterior pole portion NPAs are picked out in this manner, enabling the precision of detecting posterior pole portion NPAs to be raised.

Moreover, eliminating misdetected posterior pole portion NPAs enables the extraction of only posterior pole portion NPAs that are actual non perfusion areas requiring photocoagulation treatment.

Next, explanation follows regarding UWF-NPA image processing, with reference to FIG. 11. UWF-NPAs are regions where no retinal blood vessels are present at positions at the peripheral portion of the fundus.

As illustrated in FIG. 11, at step S400 the image processing control section 206 performs image emphasis processing on the acquired FA image to emphasize the vascular portions thereof. This is processing to make the blood vessels, including capillaries, more prominent in order to predict UWF-NPAs with good precision.

At step S402 the image processing control section 206 performs blood vessel binarization processing to binarize the emphasized vascular image in which vascular portions have been emphasized. At step S404, the image processing control section 206 performs distance image creation processing to create a distance image using the binary vascular image resulting from binarizing the emphasized vascular image in which the vascular portions have been emphasized. The distance image is an image in which the brightness becomes greater as the distance from the edge of a line segment in the binary image (corresponding to a vascular portion) increases.

At step S406, the image processing control section 206 performs binarization processing to binarize the distance image. The binarization processing of the distance image performed here results in the distance image being binarized to give a binarized distance image in the fundus peripheral portion, this means that the fundus peripheral portion is peripheral of the fundus posterior pole portion, are converted into white regions (in some cases white regions also remain at parts of the posterior pole portion).

At step S408, the image processing control section 206 performs processing to remove regions containing a predetermined fixed number of pixels or fewer. This processing is processing performed on the binarized distance image resulting from binarizing the distance image to convert white regions that are regions containing the fixed number of pixels or fewer into black regions. More specifically, plural white pixels are extracted from the binarized distance image, and a single or plural regions having a surface area of contiguous white pixels of a prescribed surface area or smaller are converted into regions of contiguous black pixels. The binarized distance image includes white regions representing vascular portions at the fundus posterior pole portion, and at the fundus peripheral portion peripheral to the fundus posterior pole portion. Predetermining the size, for example the number of pixels in a width direction, of vascular portions at the fundus posterior pole portion as a fixed number of pixels enables the vascular portions at the fundus posterior pole portion to be converted into black regions in the binarized distance image. Accordingly, white regions at the fundus peripheral portion accordingly remain in the binarized distance image.

At step S410, the image processing control section 206 extracts the outlines of the UWF-NPAs by extracting the outlines of any white regions remaining in the binarized distance image after removal of the white regions containing the fixed number of pixels or fewer. The outlines of the UWF-NPAs are images to be displayed superimposed on the FA image so as to enable the positions of the UWF-NPAs in the FA image to be easily recognized.

The image processing relating to UWF-NPAs is performed in the above manner.

Next, a display method for the non perfusion areas (NPAs) will be described in detail with reference to the screen 500 of the display 156 of the image viewer 150 illustrated in FIG. 12 and FIG. 13.

Figure 12:
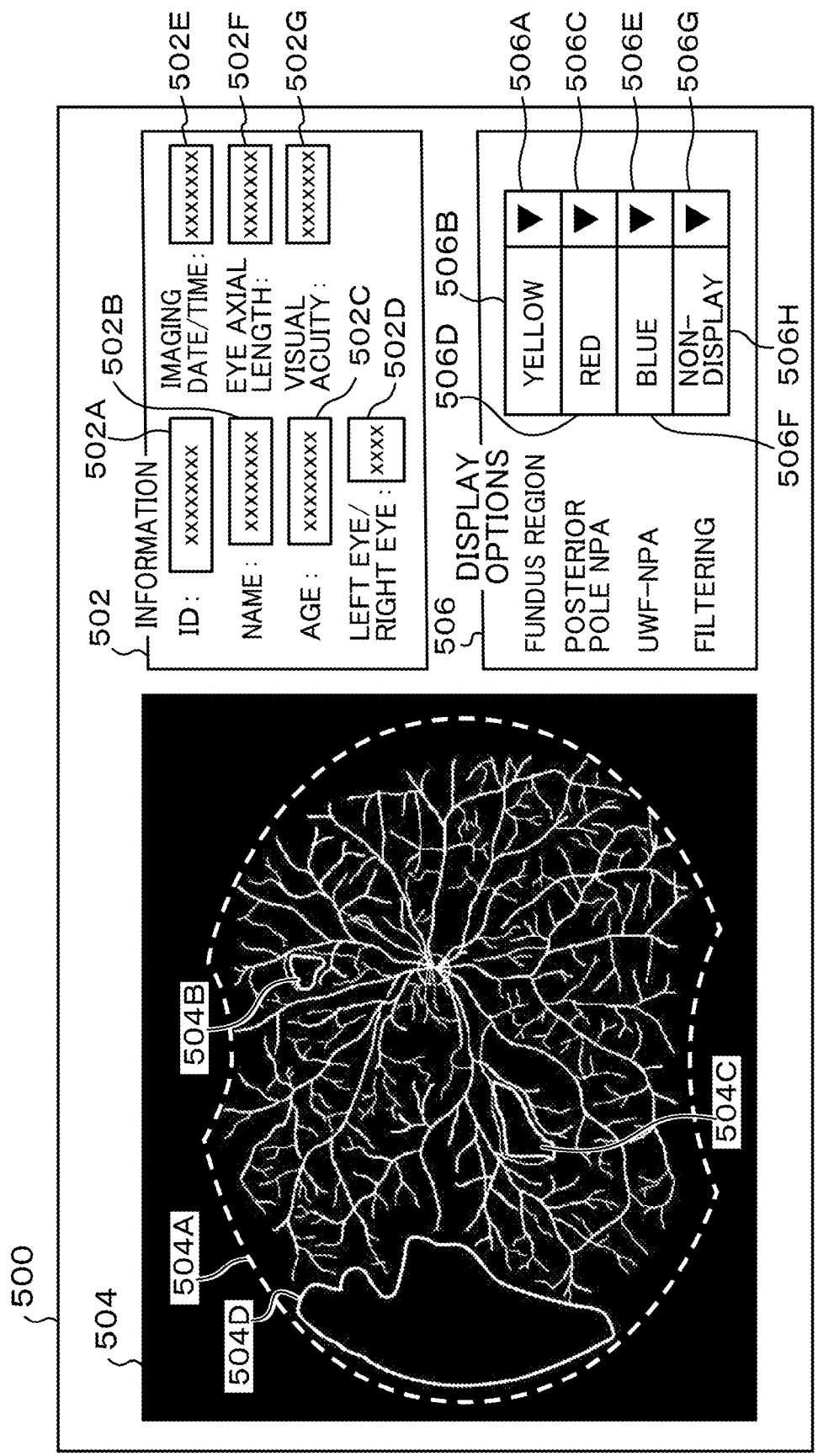
FIG. 12 is a diagram illustrating a display screen displayed on an image viewer display according to an exemplary embodiment.
Figure 13:
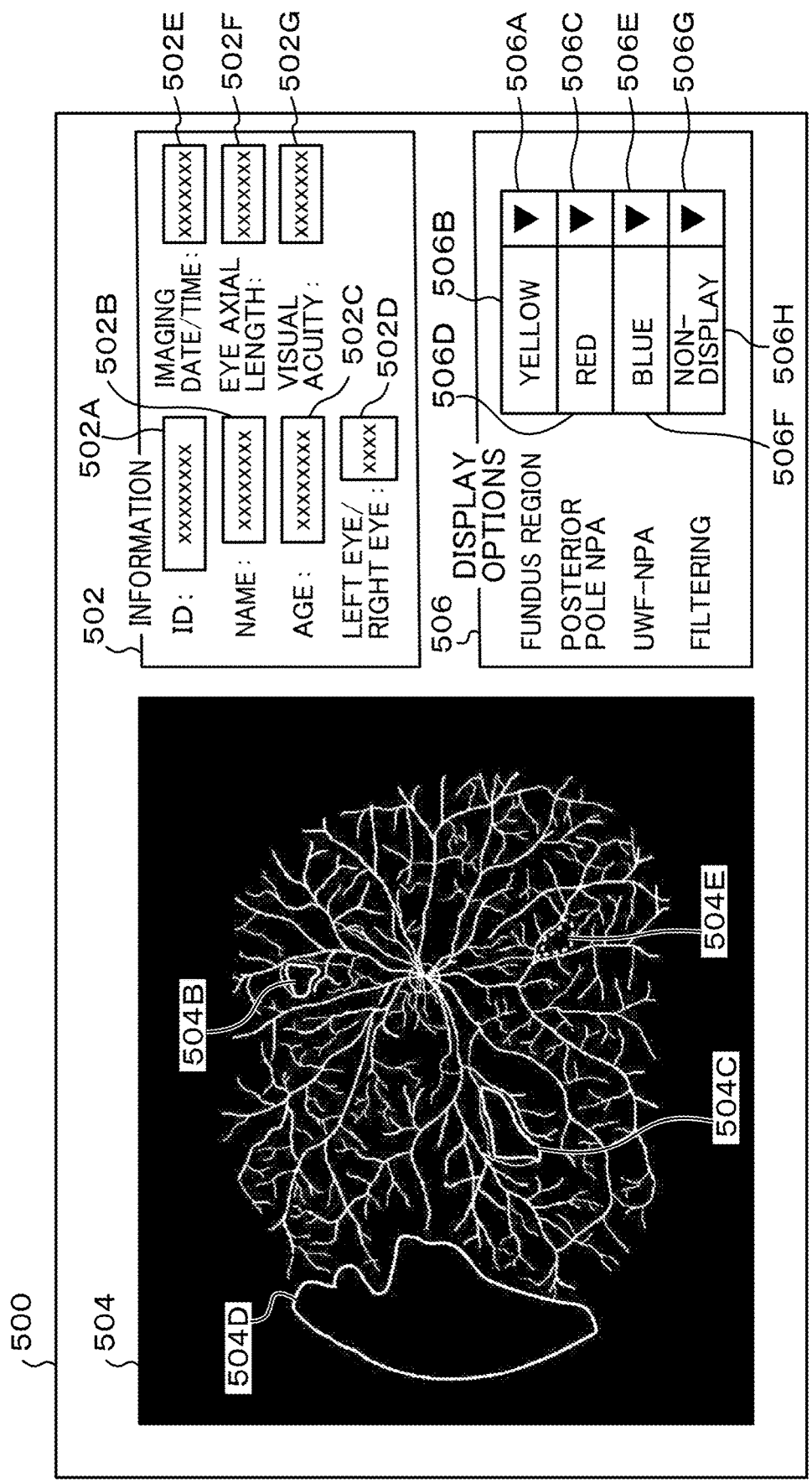
FIG. 13 is a diagram illustrating a display screen displayed on an image viewer display according to an exemplary embodiment.

FIG. 12 and FIG. 13 are examples of images relating to fundus images of the examined eye 12 displayed by executing the "image display method" of technology disclosed herein.

When a patient ID is input by an operator performing a fundus image examination, the image viewer 150 issues a command to the management server 140 to output patient information. The management server 140 reads the patient information associated with the patient ID. The management server 140 then reads a FA image, and performs image processing thereon as explained with reference to FIG. 7. The outline image of the fundus region, the outline images of any posterior pole NPAs, the outline images of any UWF-NPAs, and the outline images of any misdetected posterior pole portion NPAs corresponding to the obtained FA image are then saved in the storage device 154 of the management server. Moreover, an image is created in which the outline image of the fundus region subjected to the image processing, outline images of any posterior pole portion NPAs, outline images of any UWF-NPAs, and outline images of any misdetected posterior pole portion NPAs are superimposed on the FA image, a display screen for use on the image viewer 150 is generated, and image data for this display screen is sent to the image viewer 150. The display control section 104 of the image viewer 150 performs control to display the image represented by the display screen image data from the management server 140 on the display 156.

When an outline image display state, described later, is instructed by the operator, the image viewer 150 generates a display screen in response to the instruction, and issues a command to the management server 140 to output image data for the display screen. The processing section 108 of the image viewer 150 receives the image data for the display screen corresponding to the instructed outline image display state, and the display control section 104 performs control to display this image on the display 156.

In the example illustrated in FIG. 12, display contents relating to non perfusion areas (NPAs) are displayed on the screen 500 on the display 156 of the image viewer 150. The screen 500 includes a patient information display field 502, a fundus image display field 504, and an option instruction display field 506.

The patient information display field 502 includes a patient ID display field 502A, a patient name display field 502B, an age display field 502C, a target eyeball display field 502D, an imaging date/time display field 502E, an eye axial length display field 502F, and a visual acuity display field 502G. The image viewer 150 acquires the patient ID, the patient name, the age, the target eyeball, the imaging date/time, the eye axial length, and the visual acuity stored in the management server 140. The image viewer 150 respectively displays the acquired patient ID, patient name, age, target eyeball, imaging date/time, eye axial length, and visual acuity in the patient ID display field 502A, the patient name display field 502B, the target eyeball display field 502D, the imaging date/time display field 502E, the eye axial length display field 502F, and the visual acuity display field 502G.

The image viewer 150 displays the FA image corresponding to the patient in the fundus image display field 504 of the screen 500. Moreover, the image viewer 150 displays the outline images of the non perfusion areas (NPA) superimposed on the FA image in order to facilitate observation and diagnosis of the fundus of the examined eye 12.

The example illustrated in FIG. 12 illustrates a display state of a fundus region outline image 504A on the FA image, posterior pole NPA outline images 504B, 504C, and a UWF-NPA outline image 504D are displayed. The example illustrated in FIG. 13 illustrates a display state in which the fundus region outline image 504A is not displayed on the fundus region of the FA image, but the posterior pole NPA outline images 504B, 504C, the UWF-NPA outline image 504D, and a misdetected posterior pole portion NPA 504E are displayed.

The operator of the image viewer 150 (a doctor, for example) may desire to change the display state of the images being displayed in the fundus image display field 504. To do this, the option instruction display field 506 includes instruction buttons for selecting instructions regarding the display state of the images displayed in the fundus image display field 504, and includes display fields to display instruction results.

In the example illustrated in FIG. 12, the option instruction display field 506 includes a pull-down style instruction button 506A to instruct whether or not to display the outline image of the fundus region on the FA image and instruct a display color thereof, and a display field 506B to display the instruction result. The display state of the outline image of the fundus region displayed in the fundus image display field 504 may be changed by a selection instruction of the instruction button 506A by the operator of the image viewer 150 (a doctor, for example). For example, whether or not to display the outline image of the fundus region and the display color thereof is instructed by the operator by manipulating an input means such as a mouse 155M. When whether or not to display the outline image of the fundus region and the display color thereof have been instructed, the image viewer 150 displays the outline image of the fundus region as per the instructed display/non-display and display color.

The option instruction display field 506 includes a pull-down style instruction button 506C to instruct whether or not to display the outline images of posterior pole portion NPAs and instruct a display color thereof, and a display field 506D to display the instruction result. The display state of the outline images of the posterior pole portion NPAs displayed in the fundus image display field 504 may be changed by a selection instruction performed by the operator of the image viewer 150 using the instruction button 506C. For example, whether or not to display the outline images of the posterior pole portion NPAs and the display color thereof are instructed by the operator manipulating an input means such as the mouse 155M. When whether or not to display the outline images of the posterior pole portion NPAs and the display color thereof have been instructed, the image viewer 150 displays the outline images of the posterior pole portion NPAs as per the instructed display/non-display and display color.

Moreover, the option instruction display field 506 also includes a pull-down style instruction button 506E to instruct whether or not to display the outline images of UWF-NPAs and instruct a display color thereof, and a display field 506F to display the instruction result. The display state of the outline images of the UWF-NPAs displayed in the fundus image display field 504 may be changed by the operator of the image viewer 150 by a selection instruction using the instruction button 506E. For example, whether or not to display the outline images of the UWF-NPAs and the display color thereof are instructed by the operator manipulating an input means such as the mouse 155M. When whether or not to display the outline images of the UWF-NPAs and the display color thereof have been instructed, the image viewer 150 displays the outline images of the UWF-NPAs as per the instructed display/non-display and display color.

Moreover, the option instruction display field 506 also includes a pull-down style instruction button 506G to instruct whether or not to display the outline images of misdetected posterior pole portion NPAs, which are regions having a low likelihood of being a posterior pole portion NPA despite being detected as posterior pole portion NPAs, and instruct a display color thereof, and a display field 506H to display the instruction result. The display state of the outline images of the misdetected posterior pole portion NPAs displayed in the fundus image display field 504 may be changed by the operator of the image viewer 150 by a selection instruction using the instruction button 506G. For example, whether or not to display the outline images of the misdetected posterior pole portion NPAs and the display color thereof are instructed by the operator manipulating an input means such as the mouse 155M. When whether or not to display the outline images of the misdetected posterior pole portion NPAs and the display color thereof have been instructed, the image viewer 150 displays the outline images of the misdetected posterior pole portion NPAs as per the instructed display/non-display and display color.

The image viewer 150 acquires from the management server 140 the FA image, the fundus region outline images, the posterior pole portion NPA outline images, the UWF-NPA outline images, and the misdetected posterior pole portion NPA outline images. Then, from out of the fundus region outline image, the posterior pole portion NPA outline images, the UWF-NPA outline images, and the misdetected posterior pole portion NPA outline images, those outline images instructed by the operator are displayed superimposed on the FA image. Note that generation of the display image to display outline images such as the non perfusion areas (NPA) superimposed on the FA image may be performed either in the management server 140 or in the image viewer 150.

Note that display states of outline images displayed in the fundus image display field 504 of the screen 500 by the image viewer 150 are not limited to the display states illustrated in FIG. 12 and FIG. 13. For example, various changes may be made to the line thicknesses and line types of the outline images, for example by employing dotted lines and solid lines. Accordingly, the operator may adopt different colors for the respective display colors of the outline images, or may change the line types for the outline images of the fundus region, the posterior pole portion NPAs, the UWF-NPAs, and the misdetected posterior pole portion NPAs, such that the differences can be seen. Changes may also be made to both the colors and line types of the outline images.

The fundus image display field 504 of the screen 500 is displayed by the image viewer 150, and the posterior pole portion NPAs identified by the outline images of the posterior pole portion NPAs, are one type of information allowing a doctor to diagnose diabetic retinopathy, diabetic macular edema, retinal vein occlusion, or the like, and to determine or check on pathological progression or results of treatment.

Moreover, the UWF-NPAs identified by the UWF-NPA outline images are one type of information allowing a doctor to confirm an early diagnosis. For example, such information may assist an ophthalmologist in diagnosing diseases that initially manifest in the peripheral portion of the fundus, such as "pre-proliferative diabetic retinopathy", "proliferative diabetic retinopathy", "branch retinal vein occlusion", "Coats' disease", "non-infectious uveitis", and the like, and symptoms for which examination of the fundus is useful when finalizing a diagnosis.

Furthermore, the detection of posterior pole portion NPAs may assist determination of the results of treatment such as photocoagulation, and determination as to whether or not additional surgery is required.

The visualization of UWF-NPAs may assist in early diagnosis and establishing the state of progression of diabetic retinopathy and the like, and enable quantitative results of drug treatments such as with vascular endothelial growth factor (VEGF) and blood pressure control to be ascertained.

Explanation follows regarding various modified examples of the technology disclosed herein.

First Modified Example

Figure 14:
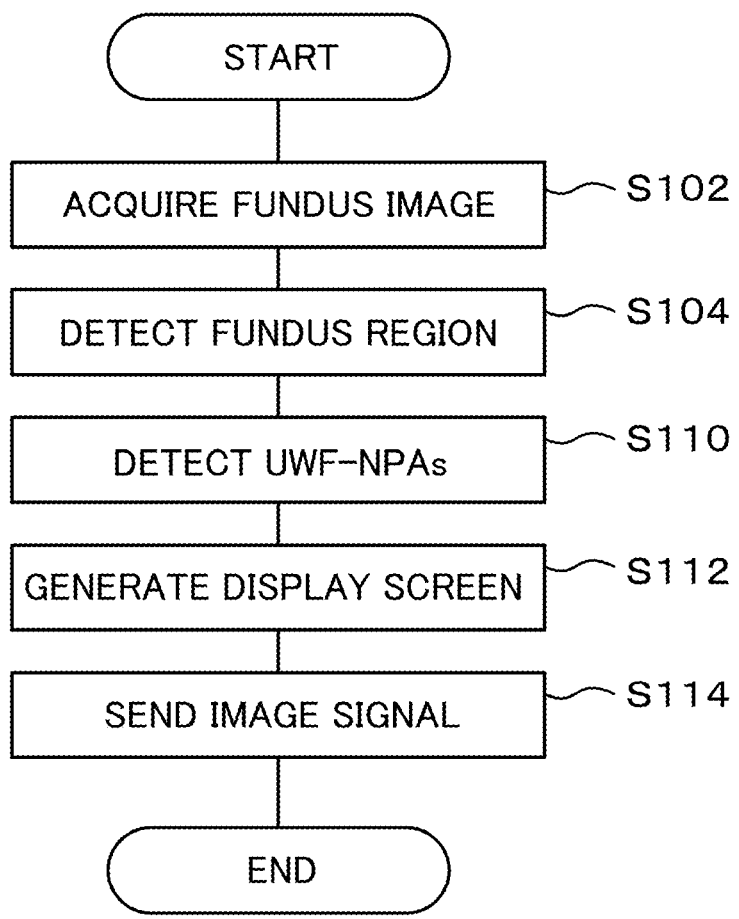
FIG. 14 is a flowchart illustrating a flow of processing according to a first modified example.

Although in the above exemplary embodiment a case has been described in which the image processing control section 206 executes posterior pole portion NPA image processing (step S106 and step S108), and UWF-NPA image processing (step S110), the technology disclosed herein is not limited thereto. For example, as illustrated in FIG. 14, the image processing control section 206 may execute the UWF-NPA image processing alone. The processing illustrated in FIG. 14 is similar to that described above, and detailed explanation thereof will be omitted.

Note that the first modified example includes the following technical content.

(1) An image processing method including a step of acquiring a fundus image, and a step of extracting a non perfusion area in a region including a periphery of a fundus region from the fundus image.

(2) An image display method including a step of acquiring a fundus image and information relating to a non perfusion area in a region including a periphery of a fundus region extracted from the fundus image, and a step of displaying the non perfusion area superimposed on the fundus image.

(3) An image processing program that causes a computer to execute the image processing method described at (1).

(4) An image display program that causes a computer to execute the image display method described at (2).

(5) An image processing device including a fundus image acquisition section configured to acquire a fundus image, and a non perfusion area extraction section configured to extract from the fundus image a non perfusion area in a region including a periphery of a fundus region.

(6) An image display device including an acquisition section configured to acquire a fundus image and information relating to a non perfusion area in a region including a periphery of a fundus region extracted from the fundus image, and a display section configured to display the non perfusion area superimposed on the fundus image.

Second Modified Example

Figure 15:
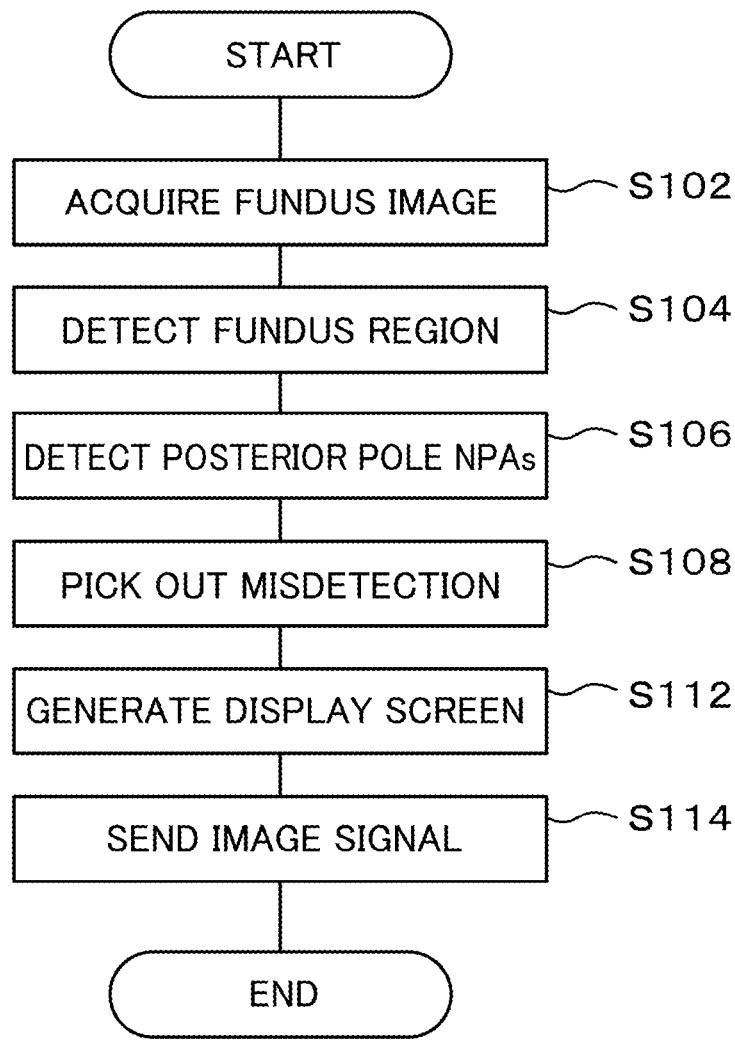
FIG. 15 is a flowchart illustrating a flow of processing according to a second modified example.

Although in the above exemplary embodiment the image processing control section 206 executes the posterior pole portion NPA image processing and the UWF-NPA image processing, and in the first modified example the image processing control section 206 executes the UWF-NPA image processing alone, the technology disclosed herein is not limited thereto. For example, as illustrated in FIG. 15, the image processing control section 206 may execute the posterior pole portion NPA image processing alone. The processing illustrated in FIG. 15 is similar to that described above and so detailed explanation thereof will be omitted.

Note that the second modified example includes the following technical content.

(7) An image processing method including a step of acquiring a fundus image, and a step of extracting a non perfusion area in a region including a center of a fundus region from the fundus image.

(8) The image processing method described at (7), further including a step of extracting a region likely to have been misdetected from out of the extracted non perfusion areas, and a step of excluding the region likely to have been misdetected from the extracted first non perfusion areas.

(9) An image display method including a step of acquiring a fundus image and information relating to a non perfusion area in a region including a center of a fundus region extracted from the fundus image, and a step of displaying the non perfusion area superimposed on the fundus image.

(10) An image processing program that causes a computer to execute the image processing method described at (7) or (8).

(11) An image display program that causes a computer to execute the image display method described at (9).

(12) An image processing device including a fundus image acquisition section configured to acquire a fundus image, and a non perfusion area extraction section configured to extract from the fundus image a non perfusion area in a region including a posterior pole portion of a fundus region.

(13) An image display device including an acquisition section configured to acquire a fundus image and information relating to a non perfusion area a non perfusion area in a region including a posterior pole portion of a fundus region extracted from the fundus image, and a display section configured to display the non perfusion area superimposed on the fundus image.

Third Modified Example

Although in the exemplary embodiment described above the management server 140 executes the image processing program illustrated in FIG. 7 in advance, the technology disclosed herein is not limited thereto. A configuration may be adopted in which the image viewer 150 transmits an image processing command to the management server 140, and the management server 140 executes the image processing program of FIG. 6 in response to this command.

Fourth Modified Example

In the exemplary embodiment described above, explanation has been given regarding examples in which a fundus image having an internal illumination angle of approximately 200° is acquired by the ophthalmic device 110. The technology disclosed herein is not limited thereto, and the technology disclosed herein may also be applied in a configuration in which a fundus image having an internal illumination angle of 100° or less is captured by an ophthalmic device, or in a configuration in which a montage image synthesized from plural fundus images is employed.

Fifth Modified Example

Although in the exemplary embodiment described above the fundus image is captured by the ophthalmic device 110 provided with an SLO imaging unit, the technology disclosed herein may also be applied to a configuration in which an image obtained by OCT angiography is employed.

Sixth Modified Example

In the exemplary embodiment described above, the management server 140 executes the image processing program. The technology disclosed herein is not limited thereto. For example, the ophthalmic device 110 or the image viewer 150 may execute the image processing program.

Seventh Modified Example

Although explanation has been given in the exemplary embodiment described above regarding an example in which the ophthalmic system 100 is provided with the ophthalmic device 110, the laser treatment device 120, the management server 140, and the image viewer 150, the technology disclosed herein is not limited thereto. For example, as a first example, a configuration may be adopted in which the laser treatment device 120 is omitted and the ophthalmic device 110 further incorporates the functionality of the laser treatment device 120. Alternatively, as a second example, a configuration may be adopted in which the ophthalmic device 110 further incorporates the functionality of at least one out of the management server 140 or the image viewer 150. For example, the management server 140 may be omitted in cases in which the ophthalmic device 110 includes the functionality of the management server 140. In such cases, the image processing program is executed by the ophthalmic device 110 or the image viewer 150. Alternatively, the image viewer 150 may be omitted in cases in which the ophthalmic device 110 includes the functionality of the image viewer 150. As a third example, a configuration may be adopted in which the management server 140 is omitted, and the image viewer 150 executes the functionality of the management server 140.

Eighth Modified Example

Although in the above exemplary embodiment explanation has been given regarding a case in which posterior pole portion NPAs are detected by the image processing control section 206 executing the processing illustrated in FIG. 9, technology disclosed herein is not limited thereto. For example, the posterior pole portion NPAs may be detected by the processing illustrated in FIG. 16.

Figure 16:
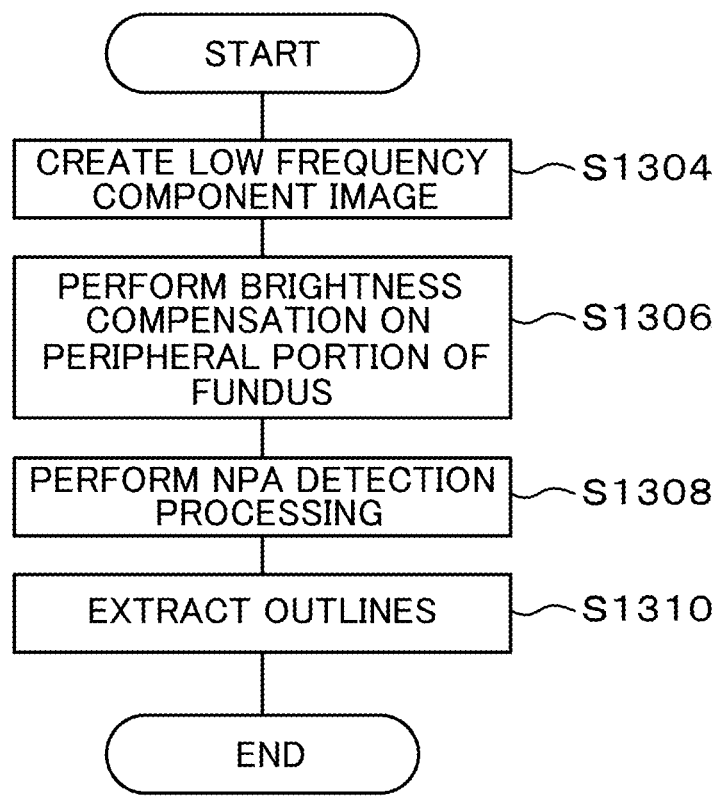
FIG. 16 is a flowchart illustrating a flow of processing according to an eighth modified example.

Explanation follows regarding such posterior pole portion NPA image processing, with reference to FIG. 16.

As illustrated in FIG. 16, at step S1304, processing is performed on the acquired FA image to remove the retinal blood vessels. A Gaussian filter is then employed to remove high frequency components from the image from which the retinal blood vessels have been processed out to create a low frequency component image.

The image processing control section 206 then, at step S1306, performs brightness compensation on the peripheral portion of the fundus by subtracting the low frequency component image from the FA image.

The image processing control section 206 then performs NPA detection processing at step S1308. More specifically, plural pixels having a first darkness or lower are extracted from the fundus image obtained at step S1306 and having brightness-compensated fundus peripheral portions, and a single or plural regions having a surface area of contiguous dark pixels of the first darkness or lower of a prescribed surface area or larger are detected as posterior pole portion NPAs. Then at step S1310, the image processing control section 206 extracts outlines of the detected posterior pole portion NPAs, and the processing is then ended.

As described above, in the eighth modified example, image processing relating to posterior pole portion NPAs is performed. In contrast to the posterior pole portion NPA processing illustrated in FIG. 9, there is no need to perform the extraction processing of step S308 and step S310, thereby enabling faster processing and thus enabling the number of fundus images processed per unit time to be increased.

Ninth Modified Example

Although the exemplary embodiment described above is configured such that the screen 500 displayed on the image viewer 150 includes the outline image of the fundus region, the outline images of posterior pole NPAs, the outline images of UWF-NPAs, and the outline images of misdetected posterior pole portion NPAs superimposed on the FA image, the technology disclosed herein is not limited thereto. For example, a configuration may be adopted in which the image displayed includes the outline image of the fundus region, the outline images of posterior pole NPAs, the outline images of UWF-NPAs, and the outline images of misdetected posterior pole portion NPAs superimposed on a face-on image (en-face image) obtained from a color fundus image and OCT data. In such cases, positional alignment is performed between the FA image and the other image, such as the color fundus image, and the outline images are then displayed superimposed at appropriate positions on the color fundus image.

Other Modified Examples

The data processing as explained in the exemplary embodiment described above is merely exemplary. Obviously, unnecessary steps may be omitted, new steps may be added, or the processing sequence may be rearranged within a range not departing from the spirit of the present disclosure.

Although explanation has been given in the exemplary embodiment described above regarding an example in which a computer is employed to implement data processing using a software configuration, the technology disclosed herein is not limited thereto. For example, instead of a software configuration employing a computer, the data processing may be executed solely by a hardware configuration such as a field programmable gate array (FPGA) or an application specific integrated circuit (ASIC). Alternatively, a configuration may be adopted in which some processing out of the data processing is executed by a software configuration, and the remaining processing is executed by a hardware configuration. Explanation of the Reference Numerals

The invention claimed is:

1. An image processing method comprising:
acquiring a fundus image;
extracting a first non perfusion area, by performing a first image processing in a first region of a fundus posterior pole portion, from the fundus image; and
extracting a second non perfusion area, by performing a second image processing, which is different from the first image processing, in a second region, which is a peripheral region of the fundus posterior pole portion, from the fundus image,
wherein, in the extracting of the second non perfusion area, a region that is a predetermined distance or more away from blood vessels on a fundus extracted from the fundus image is extracted as the second non perfusion area.

2. The image processing method of claim 1, further comprising:
extracting a third non perfusion area likely to have been misdetected among extracted first non perfusion areas; and
excluding the third non perfusion area from the extracted first non perfusion areas.

3. The image processing method of claim 1, wherein the fundus image is a fluoroscopic fundus image or an OCT image acquired by optical coherence tomography.

4. A non-transitory computer readable storage medium storing an image processing program executable by a computer to perform the image processing method of claim 1.

5. The image processing method of claim 1 wherein
in the extracting of the first non perfusion area, a region along the blood vessels on the fundus extracted from the fundus image and a region equal to or below a predetermined threshold is extracted as the first non perfusion area.

6. The image processing method of claim 5, wherein
in the extracting of the first non perfusion area, an average value of pixel values determined from at least one of brightness, saturation, or hue of a plurality of first non perfusion areas extracted from the fundus image is set as the threshold.

7. An image processing device comprising:
a fundus image acquisition section, of a processor, configured to acquire a fundus image;
a first non perfusion area extraction section, of the processor, configured to extract, a first non perfusion area, by performing a first image processing in a first region of a fundus posterior pole portion, from the fundus image; and
a second non perfusion area extraction section, of the processor, configured to extract, a second non perfusion area, by performing a second image processing, which is different from the first image processing, in a second region, which is a peripheral region of the fundus posterior pole portion, from the fundus image,
wherein the second non perfusion area extraction section extracts a region that is a predetermined distance or more away from blood vessels on a fundus extracted from the fundus image, as the second non perfusion area.

* * * * *